(12) United States Patent
Church

(10) Patent No.: US 6,432,360 B1
(45) Date of Patent: Aug. 13, 2002

(54) REPLICA AMPLIFICATION OF NUCLEIC ACID ARRAYS

(75) Inventor: George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/143,014

(22) Filed: Aug. 28, 1998

Related U.S. Application Data

(60) Provisional application No. 60/061,511, filed on Oct. 10, 1997, now abandoned, and provisional application No. 60/076,570, filed on Mar. 2, 1998, now abandoned.

(51) Int. Cl.$^7$ .............................. G01N 15/06; C12Q 1/68
(52) U.S. Cl. .............................. 422/68.1; 422/50; 435/6; 536/22.1; 536/23.1
(58) Field of Search .................... 435/6, 810; 422/50, 422/68.1; 536/23.1, 24.1, 24.3–24.33, 25.3; 935/77.78

(56) References Cited

U.S. PATENT DOCUMENTS

| | | | | |
|---|---|---|---|---|
| 4,591,567 | A | 5/1986 | Britten et al. | 435/293 |
| 4,731,325 | A | 3/1988 | Palva et al. | 435/6 |
| 4,863,849 | A | 9/1989 | Melamede | 435/6 |
| 4,981,783 | A | 1/1991 | Augenlicht | 435/6 |
| 5,188,963 | A | 2/1993 | Stapleton | 435/299 |
| 5,302,509 | A | 4/1994 | Cheeseman | 435/6 |
| 5,306,619 | A | 4/1994 | Edwards et al. | 435/6 |
| 5,324,633 | A | 6/1994 | Fodor et al. | 435/6 |
| 5,328,825 | A | 7/1994 | Warren, III et al. | 435/6 |
| 5,382,511 | A | 1/1995 | Stapleton | 435/6 |
| 5,405,746 | A | 4/1995 | Uhlen | 435/6 |
| 5,424,186 | A | 6/1995 | Fodor et al. | 435/6 |
| 5,426,180 | A | 6/1995 | Kool | 536/25.3 |
| 5,437,976 | A | 8/1995 | Utermohlen | 435/6 |
| 5,445,934 | A | 8/1995 | Fodor et al. | 435/6 |
| 5,451,500 | A | 9/1995 | Stapleton | 435/6 |
| 5,484,702 | A | 1/1996 | Ludwig | 435/6 |
| 5,506,350 | A | 4/1996 | Bittner et al. | 536/55.3 |
| 5,510,270 | A | 4/1996 | Fodor et al. | 436/518 |
| 5,527,681 | A | 6/1996 | Holmes | 435/6 |
| 5,545,531 | A | 8/1996 | Rava et al. | 435/6 |
| 5,552,270 | A | 9/1996 | Khrapko et al. | 435/6 |
| 5,556,752 | A | 9/1996 | Lockhart et al. | 435/6 |
| 5,571,639 | A | 11/1996 | Hubbell et al. | 430/5 |
| 5,578,444 | A | 11/1996 | Edwards et al. | 435/6 |
| 5,578,832 | A | 11/1996 | Trulson et al. | 250/458.1 |
| 5,587,128 | A | 12/1996 | Wilding et al. | 422/50 |
| 5,593,839 | A | 1/1997 | Hubbell et al. | 435/6 |
| 5,599,695 | A | 2/1997 | Pease et al. | 435/91.1 |
| 5,616,478 | A | 4/1997 | Chetverin et al. | 435/91.2 |
| 5,631,134 | A | 5/1997 | Cantor | 435/6 |
| 5,641,658 | A | 6/1997 | Adams et al. | 435/91.2 |
| 5,653,939 | A | 8/1997 | Hollis et al. | 422/50 |
| 5,795,714 | A | * 8/1998 | Cantor et al. | 435/6 |

FOREIGN PATENT DOCUMENTS

| | | |
|---|---|---|
| WO | WO 93/17126 | 9/1993 |
| WO | WO 96/28457 | 9/1996 |
| WO | WO 96/36731 | 11/1996 |
| WO | WO 97/09449 | 3/1997 |
| WO | WO 97/10365 | 3/1997 |
| WO | WO 98/44151 | 10/1998 |
| WO | WO 98/44152 | 10/1998 |

OTHER PUBLICATIONS

Maniatis et al. *Molecular Cloning* [publ. by Cold Spring Harbor Laboratory, Cold Spring Harbor, NY, USA], 1982.*
Malpiéce et al., 1984, Experientia, 40: 483–485.

* cited by examiner

Primary Examiner—Ardin H. Marschel
(74) Attorney, Agent, or Firm—Banner & Witcoff, Ltd.

(57) ABSTRACT

A method of producing a plurality of a nucleic acid array, comprising, in order, the steps of amplifying in situ nucleic acid molecules of a first randomly-patterned, immobilized nucleic acid array comprising a heterogeneous pool of nucleic acid molecules affixed to a support, transferring at least a subset of the nucleic acid molecules produced by such amplifying to a second support, and affixing the subset so transferred to the second support to form a second randomly-patterned, immobilized nucleic acid array, wherein the nucleic acid molecules of the second array occupy positions that correspond to those of the nucleic acid molecules from which they were amplified on the first array, so that the first array serves as a template to produce a plurality, is disclosed.

39 Claims, No Drawings

US 6,432,360 B1

REPLICA AMPLIFICATION OF NUCLEIC ACID ARRAYS

The application claims the benefit of U.S. Provisional Application No. 60/061,511, filed Oct. 10, 1997; abandoned; and U.S. Provisional Application No. 60/076,570, filed Mar. 2, 1998; abandoned.

This invention was supported by DOE Grant No. DEFG02-87ER-60565 and the government bas certain rights to the invention.

FIELD OF THE INVENTION

The invention relates in general to the reproducible, mass-production of nucleic acid arrays.

BACKGROUND OF THE INVENTION

Arrays of nucleic acid molecules are of enormous utility in facilitating methods aimed at genomic characterization (such as polymorphism analysis and high-throughput sequencing techniques), screening of clinical patients or entire pedigrees for the risk of genetic disease, elucidation of protein/DNA- or protein/protein interactions or the assay of candidate pharmaceutical compounds for efficacy; however, such arrays are both labor-intensive and costly to produce by conventional methods. Highly ordered arrays of nucleic acid fragments are known in the art (Fodor et al., U.S. Pat. No. 5,510,270; Lockhart et al., U.S. Pat. No. 5,556,752). Chetverin and Kramer (WO 93/17126) are said to disclose a highly ordered array which may be amplified.

U.S. Pat. No. 5,616,478 of Chetverin and Chetverina reportedly claims methods of nucleic acid amplification, in which pools of nucleic acid molecules are positioned on a support matrix to which they are not covalently linked. Utermohlen (U.S. Pat. No. 5,437,976) is said to disclose nucleic acid molecules randomly immobilized on a reusable matrix.

There is need in the art for improved methods of nucleic acid array design and production.

SUMMARY OF THE INVENTION

The invention provides a method of producing a plurality of a nucleic acid array, comprising, in order, the steps of amplifying in situ nucleic acid molecules of a first randomly-patterned, immobilized nucleic acid array comprising a heterogeneous pool of nucleic acid molecules affixed to a support, transferring at least a subset of the nucleic acid molecules produced by such amplifying to a second support, and affixing the subset so transferred to the second support to form a second randomly-patterned, immobilized nucleic acid array, wherein the nucleic acid molecules of the second array occupy positions that correspond to those of the nucleic acid molecules from which they were amplified on the first array, so that the first array serves as a template to produce a plurality.

As used herein in reference to nucleic acid arrays, the term "plurality" is defined as designating two or more such arrays, wherein a first (or "template") array plus a second array made from it comprise a plurality. When such a plurality comprises more than two arrays, arrays beyond the second array may be produced using either the first array or any copy of it as a template.

As used herein, the terms "randomly-patterned" or "random" refer to a non-ordered, non-Cartesian distribution (in other words, not arranged at pre-determined points along the x- and y axes of a grid or at defined 'clock positions', degrees or radii from the center of a radial pattern) of nucleic acid molecules over a support, that is not achieved through an intentional design (or program by which such a design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon.

As used herein, the terms "immobilized" or "affixed" refer to covalent linkage between a nucleic acid molecule and a support matrix.

As used herein, the term "array" refers to a heterogeneous pool of nucleic acid molecules that is distributed over a support matrix; preferably, these molecules differing in sequence are spaced at a distance from one another sufficient to permit the identification of discrete features of the array.

As used herein, the term "heterogeneous" is defined to refer to a population or collection of nucleic acid molecules that comprises a plurality of different sequences; it is contemplated that a heterogeneous pool of nucleic acid molecules results from a preparation of RNA or DNA from a cell which may be unfractionated or partially-fractionated.

An "unfractionated" nucleic acid preparation is defined as that which has not undergone the selective removal of any sequences present in the complement of RNA or DNA, as the case may be, of the biological sample from which it was prepared. A nucleic acid preparation in which the average molecular weight has been lowered by cleaving the component nucleic acid molecules, but which still retains all sequences, is still "unfractionated" according to this definition, as it retains the diversity of sequences present in the biological sample from which it was prepared.

A "partially-fractionated" nucleic acid preparation may have undergone qualitative size-selection. In this case, uncleaved sequences, such as whole chromosomes or RNA molecules, are Us selectively retained or removed based upon size. In addition, a "partially-fractionated" preparation may comprise molecules that have undergone selection through hybridization to a sequence of interest; alternatively, a "partially-fractionated" preparation may have had undesirable sequences removed through hybridization. It is contemplated that a "partially-fractionated" pool of nucleic acid molecules will not comprise a single sequence that has been enriched after extraction from the biological sample to the point at which it is pure, or substantially pure.

In this context, "substantially pure" refers to a single nucleic acid sequence that is represented by a majority of nucleic acid molecules of the pool. Again, this refers to enrichment of a sequence in vitro; obviously, if a given sequence is heavily represented in the biological sample, a preparation containing it is not excluded from use according to the invention.

As used herein, the term "biological sample" refers to a whole organism or a subset of its tissues, cells or component parts (e.g. fluids). "biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as nucleic acid molecules.

As used herein, the term "organism" refers to all cellular life-forms, such as prokaryotes and eukaryotes, as well as non-cellular, nucleic acid-containing entities, such as bacteriophage and viruses.

As used herein, the term "feature" refers to each nucleic acid sequence occupying a discrete physical location on the array; if a given sequence is represented at more than one such site, each site is classified as a feature. In this context, the term "nucleic acid sequence" may refer either to a single nucleic acid molecule, whether double or single-stranded, to a "clone" of amplified copies of a nucleic acid molecule present at the same physical location on the array or to a replica, on a separate support, of such a clone.

As used herein, the term "amplifying" refers to production of copies of a nucleic acid molecule of the array via repeated rounds of primed enzymatic synthesis; "in situ amplification" indicates that such amplifying takes place with the template nucleic acid molecule positioned on a support according to the invention, rather than in solution.

As used herein, the term "support" refers to a matrix upon which nucleic acid molecules of a nucleic acid array are immobilized; preferably, a support is semi-solid.

As used herein, the term "semi-solid" refers to a compressible matrix with both a solid and a liquid component, wherein the liquid occupies pores, spaces or other interstices between the solid matrix elements.

As used herein in reference to the physical placement of nucleic acid molecules or features and/or their orientation relative to one another on an array of the invention, the terms "correspond" or "corresponding" refer to a molecule occupying a position on a second array that is either identical to- or a mirror image of the position of a molecule from which it was amplified on a first array which served as a template for the production of the second array, or vice versa, such that the arrangement of features of the array relative to one another is conserved between arrays of a plurality.

As implied by the above statement, a first and second array of a plurality of nucleic acid arrays according to the invention may be of either like or opposite chirality, that is, the patterning of the nucleic acid arrays may be either identical or mirror-imaged.

As used herein, the term "replica" refers to any nucleic acid array that is produced by a printing process according to the invention using as a template a first randomly-patterned immobilized nucleic acid array.

In a preferred embodiment, the method further comprises the step of after the step of transferring at least a subset of the nucleic acid molecules produced by amplifying the molecules of the first array to a second support of repeating that step, such that another subset of the nucleic acid molecules produced by amplifying the molecules of the first array are transferred and affixed to an additional second support.

Preferably, after the step of transferring amplified nucleic acid molecules to a second support, the nucleic acid molecules remaining on the first support are amplified prior to repeating the transferring of amplified nucleic acid molecules to an additional second support.

In another preferred embodiment, the method further comprises, after the step of transferring at least a subset of the nucleic acid molecules produced by amplifying the molecules of the first array to a second support, the step of transferring and affixing at least a subset of the molecules transferred to the second support to a third support.

Preferably, the method further comprises the step of amplifying the nucleic acid molecules of the second array.

It is preferred that the pool of nucleic acid molecules is prepared from RNA or DNA.

It is additionally preferred that pool of nucleic acid molecules comprises cDNA or genomic DNA.

Preferably, the pool of nucleic acid molecules is a library.

In a preferred embodiment, the pool of nucleic acid molecules is prepared by cloning genomic DNA or cDNA into a cloning site on a nucleic acid vector and subsequently cleaving the nucleic acid molecules from the vector, wherein the cloning site is flanked on either side by oligonucleotide sequences that will remain linked to the nucleic acid molecules after cleaving.

It is preferred that the oligonucleotide sequences comprise recognition sites for a restriction enzyme(s), and particularly preferred that subsequent cleavage of the nucleic acid molecules of the library to which the sites are linked with the enzyme(s) results in the release of pairs of oligonucleotide primers that comprise sequences unique to either end of each member of the library.

Preferably, the recognition sites are those of type IIS restriction enzymes.

As used herein, the term "type IIS" refers to a restriction enzyme that cuts at a site remote from its recognition sequence. Such enzymes are known to cut at a distances from their recognition sites ranging from 0 to 20 base pairs.

It is preferred that the support is semi-solid.

Preferably, the semi-solid support is selected from the group that includes polyacrylamide, cellulose, polyamide (nylon) and cross-linked agarose, -dextran and -polyethylene glycol.

It is particularly preferred that amplifying of nucleic acid molecules of is performed by polymerase chain reaction (PCR).

Preferably, affixing of nucleic acid molecules to the support is performed using a covalent linker that is selected from the group that includes oxidized 3-methyl uridine, an acrylyl group and hexaethylene glycol.

It is also contemplated that affixing of nucleic acid molecules to the support is performed via hybridization of the members of the pool to nucleic acid molecules that are covalently bound to the support.

Preferably, the nucleic acid molecules bound to the support are synthetic oligonucleotides.

As used herein in this context, the term synthetic oligonucleotide refers to a short (10 to 1,000 nucleotides in length), double- or single-stranded nucleic acid molecule that is chemically synthesized or is the product of a biological system such as a product of primed or unprimed enzymatic synthesis.

It is preferred that the transferring of nucleic acid molecules from the first array to the second support comprises contacting the first array with a support, such that at least a subset of the nucleic acid molecules produced by amplifying are transferred to the support.

In another preferred embodiment, the transferring comprises contacting the first array with a carrier selected from the group that includes a cylindrical roller, a stamping device, a membrane and a support, such that at least a subset of the nucleic acid molecules produced by amplifying are transferred to the carrier, and subsequently contacting the carrier with a support.

The present invention also encompasses a plurality of a nucleic acid array, wherein the plurality comprises a first template randomly-patterned, immobilized nucleic acid array comprising a pool of nucleic acid molecules randomly immobilized on a support, and a second randomly-patterned, immobilized nucleic acid array, wherein the nucleic acid molecules of the second array are nucleic acid amplification products of the pool and wherein the nucleic acid molecules of the second array occupy positions on the second array that correspond to those of the nucleic acid molecules from which they were amplified on the first array.

Another aspect of the present invention is a method for determining the sequential order of genetic elements of a chromosome, comprising providing an immobilized nucleic acid array, comprising the steps of providing an immobilized chromosome, amplifying the nucleic acid sequences of the chromosome, contacting the amplified sequences with a semi-solid support, such that a subset of nucleic acid molecules produced by amplifying are retained by the support, and covalently affixing the molecules so retained to the support to form a first immobilized nucleic acid array, wherein the positions of the members of the array correspond to the positions of the DNA sequences from which they were amplified on the chromosome, and determining the order of genetic elements on the chromosome, wherein ordering comprises identifying the features of the array, wherein the position of a first feature relative that of a second feature on the array corresponds to the position of a first genetic element relative to that of a second genetic element on the chromosome.

It is preferred that the amplifying is performed by PCR.

Preferably, identifying is performed using sequencing by hybridization (SBH), quantitative incremental fluorescent nucleotide addition sequencing (QIFNAS) or stepwise ligation and cleavage.

In a preferred embodiment, the method further comprises the steps after contacting the amplified sequences of the chromosome with a support of amplifying the molecules of the first array by PCR and contacting the first array with a second support, such that at least a subset of the amplified nucleic acid molecules are transferred to the support, and covalently affixing the nucleic acid molecules to the second support to form a second immobilized nucleic acid array, wherein the positions of the members of the second array correspond to their positions on the first array.

Another aspect of the present invention is a method for localizing RNA molecules within a cell or a tissue section, comprising providing an immobilized nucleic acid array, comprising the steps of providing an immobilized cell or a tissue section, reverse transcribing RNA molecules of the cell or tissue section to produce an array of features comprising reverse transcripts, contacting the array with a support, such that at least a subset of reverse transcripts are retained by the support, covalently affixing the reverse transcripts to the support to form an immobilized nucleic acid array, and localizing the RNA molecules, comprising identifying the features of the array, wherein the positions of features on the array correspond to the positions of the RNA molecules in the cell or tissue section.

It is preferred that the method further comprises the step of amplifying the reverse transcripts.

It is additionally preferred that the amplifying is performed by PCR.

Preferably, the identifying is performed using sequencing by hybridization (SBH), quantitative incremental fluorescent nucleotide addition sequencing (QIFNAS) or stepwise ligation and cleavage.

In a preferred embodiment, the method further comprises the steps after contacting the reverse transcripts with a support of amplifying the molecules of the first array by PCR and contacting the first array with a second support, such that at least a subset of the amplified nucleic acid molecules are transferred to the support, and covalently affixing the nucleic acid molecules to the second support to form a second immobilized nucleic acid array, wherein the positions of the members of the second array correspond to the positions of the molecules from which they were amplified on the first array.

The invention also encompasses a method of obtaining a plurality of immobilized nucleic acid arrays, wherein the arrays of the plurality are derived from different nucleic acid pools, comprising the steps of providing a first immobilized nucleic array acid comprising a first pool of nucleic acid molecules that have linked to both ends oligonucleotide sequences each comprising a restriction enzyme(s) recognition site, such that cleavage of the nucleic acid molecules of the pool with the enzyme(s) results in the release of pairs of oligonucleotide primers that comprise sequences unique to either end of each member of the pool, amplifying by PCR the nucleic acid molecules of the array, contacting the first immobilized nucleic acid array with a support, such that at least a subset of nucleic acid molecules produced by amplifying are transferred to the support, covalently affixing the nucleic acid molecules to the support to form a replica of the first immobilized nucleic acid array, wherein the positions of nucleic acid molecules on the replica correspond to the positions of the nucleic acid molecules of the first array from which they were amplified, cleaving the nucleic acid molecules of the replica with the restriction enzyme(s), thereby forming an array of immobilized oligonucleotide primers that comprise sequences unique to either end of each feature of the first nucleic acid array, washing from the oligonucleotide primers the nucleic acid fragments released from them by the cleaving, contacting the primers with a second pool of nucleic acid molecules under conditions that permit hybridization of the nucleic acid molecules that are complementary, such that hybridization occurs between the oligonucleotide primers and the nucleic acid molecules of the second nucleic acid pool, amplifying the nucleic acid molecules of the second pool so hybridized to the primers, wherein the immobilized oligonucleotide primers to which they are hybridized serve to prime the amplifying, thereby forming an immobilized array of nucleic acid molecules of the second pool.

Preferably, the amplifying is performed by PCR.

It is preferred that cycles of the steps of contacting the first immobilized nucleic acid array with a support, such that at least a subset of nucleic acid molecules produced by amplifying are transferred to the support, covalently affixing the nucleic acid molecules to the support to form a replica of the first immobilized nucleic acid array, wherein the positions of nucleic acid molecules on the replica correspond to the positions of the nucleic acid molecules of the first array from which they were amplified, cleaving the nucleic acid molecules of the replica with the restriction enzyme(s), thereby forming an array of immobilized oligonucleotide primers that comprise sequences unique to either end of each feature of the first nucleic acid array, washing from the oligonucleotide primers the nucleic acid fragments released from them by the cleaving, contacting primers with a second pool of nucleic acid molecules under conditions that permit hybridization of the nucleic acid molecules that are complementary, such that hybridization occurs between the oligonucleotide primers and the nucleic acid molecules of the second nucleic acid pool, amplifying the nucleic acid molecules of the second pool so hybridized to the primers, wherein the immobilized oligonucleotide primers to which they are hybridized serve to prime the amplifying, thereby forming an immobilized array of nucleic acid molecules of the second pool are repeated.

Preferably, the method further comprises the steps, between contacting the first immobilized nucleic acid array with a support, such that at least a subset of nucleic acid molecules produced by amplifying are transferred to the support, and covalently affixing the nucleic acid molecules to the support to form a replica of the first immobilized nucleic acid array, wherein the positions of nucleic acid molecules on the replica correspond to the positions of the nucleic acid molecules of the first array from which they were amplified, of amplifying in situ the nucleic acid molecules of the replica, and contacting the replica with a second support, such that at least a subset of the nucleic acid molecules produced by the amplifying are transferred to the second support, covalently affixing the termini of the nucleic acid molecules to the blank to form a second replica of the first immobilized nucleic acid array, wherein the positions of nucleic acid molecules on the second replica correspond to the positions of the nucleic acid molecules of the replica from which they were amplified.

It is preferred that the different nucleic acid pools are obtained from different tissues of an individual organism.

It highly preferred that the different nucleic acid pools are obtained from different individual organisms of a single species.

It is also highly preferred that the different nucleic acid pools are obtained from organisms of different species.

Preferably, the first and second pools of nucleic acid molecules are libraries.

DETAILED DESCRIPTION OF THE INVENTION

The present invention is directed to the synthesis of nucleic acid array chips, methods by which such chips may be reproduced and methods by which they may be used in diverse applications relating to nucleic acid replication or amplification, genomic characterization, gene expression studies, medical diagnostics and population genetics. The nucleic acid array chips of the replica array has several advantages over the presently available methods.

Besides any known sequences or combinatorial sequence thereof, a full genome including unknown DNA sequences can be replicated according to the present invention. The size of the nucleic acid fragments or primers to be replicated can be from about 25-mer to about 9000-mer. The present invention is also quick and cost effective. It takes about only about one week from discovery of an organism to arrange the full genome sequence of the organism onto chips with about $10 per chip. In addition, the thickness of the chips is 3000 nm which provides a much higher sensitivity. The chips are compatible with inexpensive in situ PCR devices, and can be reused as many as 100 times.

The invention provides for an advance over the arrays of Chetverin and Kramer (WO 93/17126), Chetverin and Chetverina, 1997 (U.S. Pat. No. 5,616,478), and others, in that a method is herein described by which to produce a random nucleic acid array both that is covalently linked to a support (therefore extensively reusable) and that permits one to fabricate high-fidelity copies of it without returning to the starting point of the process, thereby eliminating time-consuming, expensive steps and providing for reproducible results both when the copies of the array are made and when they are used. It is evident that this method is not obvious, despite its great utility. No mention of replica plating or printing of amplimers in this context appears to have been made in oligonucleotide array patents or papers. There is no method in the prior art for generating a set of nucleic acid arrays comprising the steps of covalently linking a pool of nucleic acid molecules to a support to form a random array, amplifying the nucleic acid molecules and subsequently replicating the array.

While reproducibility of manufacture and durability are not of significant concern in the making of arrays in which the nucleic acid molecules are chemically synthesized directly on the support, they are centrally important in cases in which the molecules of the array are of natural origin (for example, a sample of mRNA from an organism). Each nucleic acid sample obtained from a natural source constitutes a unique pool of molecules; these molecules are, themselves, uniquely distributed over the surface of the support, in that the original laying out of the pattern is random. By any prior art method, an array generated from simple, random deposition of a pool of nucleic acid molecules is irreproducible; however, a set of related arrays would be of great utility, since information derived from any one copy from the replicated set would increase the confidence in the identity and/or quality of data generated using the other members of the set.

The methods provided in the present invention basically consists of 5 steps: 1) providing a pool of nucleic acid molecules, 2) plating or other transfer of the pool onto a solid support, 3) in situ amplification, 4) replica printing of the amplified nucleic acids and 5) identification of features. Sets of arrays so produced, or members thereof, then may be put to any chip affinity readout use, some of which are summarized below. The production of a set of arrays according to the invention is described in Example 1. The following examples are provided for exemplification purposes only and are not intended to limit the scope of the invention which has been described in broad terms above.

EXAMPLE 1

Production of a plurality of a nucleic acid array according to the invention

Step 1. Production of a nucleic acid pool with which to construct an array according to the invention A pool or library of n-mers (n=20 to 9000) is made by any of several methods. The pool is either amplified (e.g. by PCR) or left unamplified. A suitable in vitro amplification "vector", for example, flanking PCR primer sequences or an in vivo plasmid, phage or viral vector from which amplified molecules are excised prior to use, is used. If necessary, random shearing or enzymatic cleavage of large nucleic acid molecules is used to generate the pools if the nucleic acid molecules are amplified, cleavage is performed either before or after amplification. Alternatively, a nucleic acid sample is random primed, for example with tagged 3' terminal hexamers followed by electrophoretic size-selection. The nucleic acid is selected from genomic, synthetic or cDNA sequences (Power, 1996, *J. Hosp. Infect.*, 34:247–265; Welsh, et al., 1995, *Mutation Res.*, 338:215–229). The copied or unamplified nucleic acid fragments resulting from any of the above procedures are, if desired, fractionated by size or affinity by a variety of methods including electrophoresis, sedimentation, and chromatography (possibly including elaborate, expensive procedures or limited-quantity resources since the subsequent inexpensive replication methods can justify such investment of effort).

Pools of nucleic acid molecules are, at this stage, applied directly to the support medium (see Step 2, below). Alternatively, they are cloned into nucleic acid vectors. For example, pools composed of fragments with inherent polarity, such as cDNA molecules, are directionally cloned into nucleic acid vectors that comprise, at the cloning site, oligonucleotide linkers that provide asymmetric flanking sequences to the fragments. Upon their subsequent removal via restriction with enzymes that cleave the vector outside both the cloned fragment and linker sequences, molecules with defined (and different) sequences at their two ends are generated. By denaturing these molecules and spreading them onto a semi-solid support to which is covalently bound oligonucleotides that are complementary to one preferred flanking linker, the orientation of each molecule in the array is determined relative to the surface of the support. Such a polar array is of use for in vitro transcription/translation of the array or any purpose for which directional uniformity is preferred.

In addition to the attachment of linker sequences to the molecules of the pool for use in directional attachment to the support, a restriction site or regulatory element (such as a promoter element, cap site or translational termination signal), is, if desired, joined with the members of the pool. The use of fragments with termini engineered to comprise useful restriction sites is described below in Example 6.

Step 2. Transfer of the nucleic acid pool onto a support medium

The nucleic acid pool is diluted ("plated") out onto a semi-solid medium (such as a polyacrylamide gel) on a solid surface such as a glass slide such that amplifiable molecules are 0.1 to 100 micrometers apart. Sufficient spacing is maintained that features of the array do not contaminate one another during repeated rounds of amplification and replication. It is estimated that a molecule that is immobilized at one end can, at most, diffuse the distance of a single molecule length during each round of replication. Obviously, arrays of shorter molecules are plated at higher density than those comprising long molecules.

Immobilizing media that are of use according to the invention are physically stable and chemically inert under the conditions required for nucleic acid molecule deposition, amplification and the subsequent replication of the array. A useful support matrix withstands the rapid changes in- and extremes of temperature required for PCR and retains structural integrity under stress during the replica printing process. The support material permits enzymatic nucleic acid synthesis; if it is unknown whether a given substance will do so, it is tested empirically prior to any attempt at production of a set of arrays according to the invention. The support structure comprises a semi-solid (i.e. gelatinous) lattice or matrix, wherein the interstices or pores between lattice or matrix elements are filled with an aqueous or other liquid medium; typical pore (or 'sieve') sizes are in the range of 100 μm to 5 nm. Larger spaces between matrix elements are within tolerance limits, but the potential for diffusion of amplified products prior to their immobilization is increased. The semi-solid support is compressible, so that full surface-to-surface contact, essentially sufficient to form a seal between two supports, although that is not the object, may be achieved during replica printing. The support is prepared such that it is planar, or effectively so, for the purposes of printing; for example, an effectively planar support might be cylindrical, such that the nucleic acids of the array are distributed over its outer surface in order to contact other supports, which are either planar or cylindrical, by rolling one over the other. Lastly, a support materials of use according to the invention permits immobilizing (covalent linking) of nucleic acid features of an array to it by means enumerated below. Materials that satisfy these requirements comprise both organic and inorganic substances, and include, but are not limited to, polyacrylamide, cellulose and polyamide (nylon), as well as cross-linked agarose, dextran or polyethylene glycol.

Of the support media upon which the members of the pool of nucleic acid molecules may be anchored, one that is particularly preferred is a thin, polyacylamide gel on a glass support, such as a plate, slide or chip. A polyacrylamide sheet of this type is synthesized as follows: Acrylamide and bis-acrylamide are mixed in a ratio that is designed to yield the degree of crosslinking between individual polymer strands (for example, a ratio of 38:2 is typical of sequencing gels) that results in the desired pore size when the overall percentage of the mixture used in the gel is adjusted to give the polyacrylamide sheet its required tensile properties. Polyacrylamide gel casting methods are well known in the art (see Sambrook et al., 1989, *Molecular Cloning. A Laboratory Manual.*, 2nd Edition, Cold Spring Harbor Laboratory Press, Cold Spring Harbor, N.Y.), and one of skill has no difficulty in making such adjustments.

The gel sheet is cast between two rigid surfaces, at least one of which is the glass to which it will remain attached after removal of the other. The casting surface that is to be removed after polymerization is complete is coated with a lubricant that will not inhibit gel polymerization; for this purpose, silane is commonly employed. A layer of silane is spread upon the surface under a fume hood and allowed to stand until nearly dry. Excess silane is then removed (wiped or, in the case of small objects, rinsed extensively) with ethanol. The glass surface which will remain in association with the gel sheet is treated with γ-methacryloxypropyltrimethoxysilane (Cat. No. M6514, Sigma; St. Louis, Mo.), often referred to as 'crosslink silane', prior to casting. The glass surface that will contact the gel is triply-coated with this agent. Each treatment of an area equal to 1200 cm$^2$ requires 125 μl of crosslink silane in 25 ml of ethanol. Immediately before this solution is spread over the glass surface, it is combined with a mixture of 750 μl water and 75 μl glacial acetic acid and shaken vigorously. The ethanol solvent is allowed to evaporate between coatings (about 5 minutes under a fume hood) and, after the last coat has dried, excess crosslink silane is removed as completely as possible via extensive ethanol washes in order to prevent 'sandwiching' of the other support plate onto the gel. The plates are then assembled and the gel cast as desired.

The only operative constraint that determines the size of a gel that is of use according to the invention is the physical ability of one of skill in the art to cast such a gel. The casting of gels of up to one meter in length is, while cumbersome, a procedure well known to workers skilled in nucleic acid sequencing technology. A larger gel, if produced, is also of use according to the invention. An extremely small gel is cut from a larger whole after polymerization is complete.

Note that at least one procedure for casting a polyacrylamide gel with bioactive substances, such as enzymes, entrapped within its matrix is known in the art (O'Driscoll, 1976, *Methods Enzymol.*, 44:169–183); a similar protocol, using photo-crosslinkable polyethylene glycol resins, that permit entrapment of living cells in a gel matrix has also been documented (Nojima and Yamada, 1987, *Methods Enzymol.*, 136:380–394). Such methods are of use according to the invention. As mentioned below, whole cells are typically cast into agarose for the purpose of delivering intact chromosomal DNA into a matrix suitable for pulsed-field gel electrophoresis or to serve as a "lawn" of host cells that will support bacteriophage growth prior to the lifting of plaques according to the method of Benton and Davis (see Maniatis et al., 1982, *Molecular Cloning: A Laboratory Manual*, Cold Spring Harbor Laboratory Press, Cold Spring Harbor, N.Y.). In short, electrophoresis-grade agarose (e.g. Ultrapure; Life Technologies/Gibco-BRL; is dissolved in a physiological (isotonic) buffer and allowed to equilibrate to a temperature of 50° to 52° C. in a tube, bottle or flask. Cells are then added to the agarose and mixed thoroughly, but rapidly (if in a bottle or tube, by capping and inversion, if in a flask, by swirling), before the mixture is decanted or pipetted into a gel tray. If low-melting point agarose is used, it may be brought to a much lower temperature (down to approximately room temperature, depending upon the concentration of the agarose) prior to the addition of cells. This is desirable for some cell types; however, if electrophoresis is to follow cell lysis prior to covalent attachment of the molecules of the resultant nucleic acid pool to the support, it is performed under refrigeration, such as in a 4° to 10° C. 'cold' room.

Immobilization of nucleic acid molecules to the support matrix according to the invention is accomplished by any of several procedures. Direct immobilizing, as through use of 3'-terminal tags bearing chemical groups suitable for covalent linkage to the support, hybridization of single-stranded molecules of the pool of nucleic acid molecules to oligonucleotide primers already bound to the support or the spreading of the nucleic acid molecules on the support accompanied by the introduction of primers, added either before or after plating, that may be covalently linked to the support, may be performed. Where pre-immobilized primers are used, they are designed to capture a broad spectrum of sequence motifs (for example, all possible multimers of a given chain length, e.g. hexamers), nucleic acids with homology to a specific sequence or nucleic acids containing variations on a particular sequence motif Alternatively, the primers encompass a synthetic molecular feature common to all members of the pool of nucleic acid molecules, such as a linker sequence (see above).

Oligonucleotide primers useful according to the invention are single-stranded DNA or RNA molecules that are hybridizable to a nucleic acid template to prime enzymatic synthesis of a second nucleic acid strand. The primer is complementary to a portion of a target molecule present in a pool of nucleic acid molecules used in the preparation of sets of arrays of the invention.

It is contemplated that such a molecule is prepared by synthetic methods, either chemical or enzymatic. Alternatively, such a molecule or a fragment thereof is naturally occurring, and is isolated from its natural source or purchased from a commercial supplier. Oligonucleotide primers are 6 to 100, and even up to 1,000, nucleotides in length, but ideally from 10 to 30 nucleotides, although oligonucleotides of different length are of use.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, *Nucleic Acids Res.* 12:203, incorporated herein by reference. As a result, it is expected that a certain degree of mismatch at the priming site is tolerated. Such mismatch may be small, such as a mono-, di- or tri-nucleotide. Alternatively, it may encompass loops, which we define as regions in which mismatch encompasses an uninterrupted series of four or more nucleotides.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher $T_M$ than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are genererally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone.

Primers are designed with the above first four considerations in mind. While estimates of the relative merits of numerous sequences are made mentally, computer programs have been designed to assist in the evaluation of these several parameters and the optimization of primer sequences. Examples of such programs are "PrimerSelect" of the DNAStar™ software package (DNAStar, Inc.; Madison, Wis.) and OLIGO 4.0 (National Biosciences, Inc.). Once designed, suitable oligonucleotides are prepared by a suitable method, e.g. the phosphoramidite method described by Beaucage and Carruthers (1981, *Tetrahedron Lett.,* 22:1859–1862) or the triester method according to Matteucci et al. (1981, *J. Am. Chem. Soc.,* 103:3185), both incorporated herein by reference, or by other chemical methods using either a commercial automated oligonucleotide synthesizer or VLSIPS™ technology.

Two means of crosslinking a nucleic acid molecule to a preferred support of the invention, a polyacrylamide gel sheet, will be discussed in some detail. The first (provided by Khrapko et al., 1996, U.S. Pat. No. 5,552,270) involves the 3' capping of nucleic acid molecules with 3-methyl uridine; using this method, the nucleic acid molecules of the libraries of the present invention are prepared so as to include this modified base at their 3' ends. In the cited protocol, an 8% polyacrylamide gel (30:1, acrylamide: bis-acrylamide) sheet 30 μm in thickness is cast and then exposed to 50% hydrazine at room temperature for 1 hour; such a gel is also of use according to the present invention. The matrix is then air dried to the extent that it will absorb a solution containing nucleic acid molecules, as described below. Nucleic acid molecules containing 3-methyl uridine at their 3' ends are oxidized with 1 mM sodium periodate ($NaIO_4$) for 10 minutes to 1 hour at room temperature, precipitated with 8 to 10 volumes of 2% $LiClO_4$ in acetone and dissolved in water at a concentration of 10 pmol/μl. This concentration is adjusted so that when the nucleic acid molecules are spread upon the support in a volume that covers its surface evenly, yet is efficiently (i.e. completely) absorbed by it, the density of nucleic acid molecules of the array falls within the range discussed above. The nucleic acid molecules are spread over the gel surface and the plates are placed in a humidified chamber for 4 hours. They are then dried for 0.5 hour at room temperature and washed in a buffer that is appropriate to their subsequent use. Alternatively, the gels are rinsed in water, re-dried and stored at −20° C. until needed. It is said that the overall yield of nucleic acid that is bound to the gel is 80% and that of these molecules, 98% are specifically linked through their oxidized 3' groups.

A second crosslinking moiety that is of use in attaching nucleic acid molecules covalently to a polyacrylamide sheet is a 5' acrylyl group, which is attached to the primers used in Example 6. Oligonucleotide primers bearing such a modified base at their 5' ends may be used according to the invention. In particular, such oligonucleotides are cast directly into the gel, such that the acrylyl group becomes an integral, covalently-bonded part of the polymerizing matrix. The 3' end of the primer remains unbound, so that it is free to interact with- and hybridize to a nucleic acid molecule of the pool and prime its enzymatic second-strand synthesis.

Alternatively, hexaethylene glycol is used to covalently link nucleic acid molecules to nylon or other support matrices (Adams and Kron, 1994, U.S. Pat. No. 5,641,658). In addition, nucleic acid molecules are crosslinked to nylon via irradiation with ultraviolet light. While the length of time for which a support is irradiated as well as the optimal distance from the ultraviolet source is calibrated with each instrument used, due to variations in wavelength and transmission strength, at least one irradiation device designed specifically for crosslinking of nucleic acid molecules to hybridization membranes is commercially available (Stratalinker; Stratagene). It should be noted that in the process of crosslinking via irradiation, limited nicking of nucleic acid strand occurs; however, the amount of nicking is generally negligible under conditions such as those used in hybridization procedures. Attachment of nucleic acid molecules to the support at positions that are neither 5'- nor 3'-terminal also occurs, but it should be noted that the potential for utility of an array so crosslinked is largely uncompromised, as such crosslinking does not inhibit hybridization of oligonucleotide primers to the immobilized molecule where it is bonded to the support. The production of 'terminal' copies of an array of the invention, i.e. those that will not serve as templates for further replication, is not affected by the method of crosslinking; however, in situations in which sites of covalent linkage are, preferably, at the termini of molecules of the array, crosslinking methods other than ultraviolet irradiation are employed.

Step 3. Amplification of the nucleic acid molecules of the army

The molecules are amplified in situ (Tsongalis et al., 1994, Clinical Chemistry, 40:381–384; see also review by Long and Komminoth, 1997, Methods Mol. Biol., 71:141–161) by standard molecular techniques, such as thermal-cycled PCR (Mullis and Faloona, 1987, Methods Enzymol., 155:335–350) or isothermal 3SR (Gingeras et al., 1990, Annales de Biologie Clinique, 48(7): 498–501; Guatelli et al., 1990, Proc. Natl. Acad. Sci. U.S.A., 87:1874). Another method of nucleic acid amplification that is of use according to the invention is the DNA ligase amplification reaction (LAR), which has been described as permitting the exponential increase of specific short sequences through the activities of any one of several bacterial DNA ligases (Wu and Wallace, 1989, Genomics 4:560). The contents of this article are herein incorporated by reference.

The polymerase chain reaction (PCR), which uses multiple cycles of DNA replication catalyzed by a thermostable, DNA-dependent DNA polymerase to amplify the target sequence of interest, is well known in the art, and is presented in detail in the Examples below. The second amplification process, 3SR, is an outgrowth of the transcription-based amplification system (TAS), which capitalizes on the high promoter sequence specificity and reiterative properties of bacteriophage DNA-dependent RNA polymerases to decrease the number of amplification cycles necessary to achieve high amplification levels (Kwoh et al., 1989, Proc. Natl. Acad Sci. U.S.A., 83:1173–1177). The 3SR method comprises an isothermal, Self-Sustained Sequence Replication amplification reaction, is as follows:

Each priming oligonucleotide contains the T7 RNA polymerase binding sequence (TAATACGACTCACTATA [SEQ ID NO: 1]) and the preferred transcriptional initiation site. The remaining sequence of each primer is complementary to the target sequence on the molecule to be amplified.

The 3SR amplification reaction is carried out in 100 μl and contains the target RNA, 40 mM Tris.HCl, ph 8.1, 20 mM MgCl2, 2 mM spermidine.HCl, 5mM dithiothreitol, 80 μg/mlBSA, 1 mM dATP, 1 mM dGTP, 1 mM dTTP, 4 mMATP, 4 mM CTP, 1 mM GTP, 4 mM dTTP, 4 mM ATP, 4 mM CTP, 4 mM GTP, 4 mMUTP, and a suitable amount of oligonucleotide primer (250 ng of a 57-mer, this amount is scaled up or down, proportionally, depending upon the length of the primer sequence). Three to 6 attomoles of the nucleic acid target for the 3SR reactions is used. As a control for background, a 3SR reaction without any target ($H_2O$) is run. The reaction mixture is heated to 100° C. for 1 minute, and then rapidly chilled to 42° C. After I minute, 10 units (usually in a volume of approximately 2 μl) of reverse transcriptase, (e.g. avian myoblastosis virus reverse transcriptase, AMV-RT; Life Technologies/Gibco-BRL) is added. The reaction is incubated for 10 minutes, at 42° C. and then heated to 100° C. for 1 minute. (If a 3SR reaction is performed using a single-stranded template, the reaction mixture is heated instead to 65° C. for 1 minute.) Reactions are then cooled to 37° C. for 2 minutes prior to the addition of 4.6 μl of a 3SR enzyme mix, which contains 1.6 μl of AMV-RT at 18.5 units/μl, 1.0 μl T7 RNA polymerase (both e.g. from Stratagene; La Jolla, Calif.) at 100 units/μl and 2.0 μl E. Coli RNase H at 4 units/μl (e.g. from Gibco/Life Technologies; Gaithersburg, Md.). It is well within the knowledge of one of skill in the art to adjust enzyme volumes as needed to account for variations in the specific activities of enzymes drawn from different production lots or supplied by different manufacturers. The reaction is incubated at 37° C. for 1 hour and stopped by freezing. While the handling of reagents varies depending on the physical size of the array (which planar surface, if large, requires containment such as a tray or thermal-resistant hybridization bag rather than a tube), this method is of use to amplify the molecules of an array according to the invention.

Other methods which are of use in the amplification of molecules of the array include, but are not limited to, nucleic acid sequence-based amplification (NASBA; Compton, 1991, Nature, 350:91–92, incorporated herein by reference) and strand-displacement amplification (SDA; Walker et al., 1992, Nucleic Acids Res, 20:1691–1696, incorporated herein by reference).

Step 4. Replication of the army a. The master plate generated in steps 1 through 3 is replica-plated by any of a number of methods (reviewed by Lederberg, 1989, *Genetics*, 121(3):395–9) onto similar gel-chips. This replica is performed by directly contacting the compressible surfaces of the two gels face to face with sufficient pressure that a few molecules of each clone are transferred from the master to the replica. Such contact is brief, on the order of 1 second to 2 minutes. This is done for additional replicas from the same master, limited only by the number of molecules post-amplification available for transfer divided by the minimum number of molecules that must be transferred to achieve an acceptably faithful copy. While it is theoretically possible to transfer as little as a single molecule per feature, a more conservative approach is taken. The number of each species of molecule available for transfer never approaches a value so low as to raise concern about the probability of feature loss or to the point at which a base substitution during replication of one member of a feature could, in subsequent rounds of amplification, create a significant (detectable) population of mutated molecules that might be mistaken for the unaltered sequence, unless errors of those types are within the limits of tolerance for the application for which the array is intended. Note that differential replicative efficiencies of the molecules of the array are not as great a concern as they would be in in the case of amplification of a conventional library, such as a phage library, in solution or on a non-covalently-bound array. Because of the physical limitations on diffusion of molecules of any feature, one which is efficiently amplified cannot 'overgrow' one which is copied less efficiently, although the density of complete molecules of the latter on the array may be low. It is estimated that 10 to 100 molecules per feature are sufficient to achieve fidelity during the printing process. Typically, at least 100 to 1000 molecules are transferred.

Alternatively, the plated DNA is reproduced inexpensively by microcontact printing, or μCP, (Jackman et al, 1995, *Science*, 269(5224):664–666, 1995) onto a surface with an initially uniform (or patterned) coating of two oligonucleotides (one or both immobilized by their 5' ends) suitable for in situ amplification. Pattern elements are transferred from an elastomeric support (comparable in its physical properties to support materials that are useful according to the invention) to a rigid, curved object that is rolled over it; if desired, a further, secondary transfer of the pattern elements from the rigid cylinder or other object onto a support is performed. The surface of one or both is compliant to achieve uniform contact. For example, 30 micron thin polyacrylamide films are used for immobilizing oligomers covalently as well as for in situ hybridizations (Khrapko, et al., 1991, *DNA Sequence*, 1(6):375–88). Effective contact printing is achieved with the transfer of very few molecules of double- or single-stranded DNA from each sub-feature to the corresponding point on the recipient support.

b. The replicas are then amplified as in step 3.

c. Alternatively, a replica serves as a master for subsequent steps like step 4, limited by the diffusion of the features and the desired feature resolution.

Step 5. Identification of features of the array

Ideally, feature identification is performed on the first array of a set produced by the methods described above; however, it is also done using any array of a set, regardless of its position in the line of production. The features are sequenced by hybridization to fluorescently labeled oligomers representing all sequences of a certain length (.e.g. all 4096 hexamers) as described for Sequencing-by-Hybridization (SBH, also called Sequencing-by-Hybridization-to-an-Oligonucleotide-Matrix, or SHOM; Drmanac et al., 1993, *Science*, 260(5114):1649–52; Khrapko, et al. 1991, supra; Mugasimangalam et al., 1997, *Nucleic Acids Res.*, 25:800–805). The sequencing in step 5 is considerably easier than conventional SBH if the feature lengths are short (e.g. ss-25-mers rather than the greater than ds-300-mers used in SBH), if the genome sequence is known or if a preselection of features is used.

SBH involves a strategy of overlapping block reading. It is based on hybridization of DNA with the complete set of immobilized oligonucleotides of a certain length fixed in specific positions on a support. The efficiency of SBH depends on the ability to sort out effectively perfect duplexes from those that are imperfect (i.e. contain base pair mismatches). This is achieved by comparing the temperature-dependent dissociation curves of the duplexes formed by DNA and each of the immobilized oligonucleotides with standard dissociation curves for perfect oligonucleotide duplexes.

To generate a hybridization and dissociation curve, a $^{32}$P-labeled DNA fragment (30,000 cpm, 30 fmoles) in 1 μl of hybridization buffer (1M NaCl; 10 mM Na phosphate, pH 7.0; 0.5 mM EDTA) is pipetted onto a dry plate so as to cover a dot of an immobilized oligonucleotide. Hybridization is performed for 30 minutes at 0° C. The support is rinsed with 20 ml of hybridization buffer at 0° C. and then washed 10 times with the same buffer, each wash being performed for 1 minute at a temperature 5° C. higher than the previous one. The remaining radioactivity is measured after each wash with a minimonitor (e.g. a Mini monitor 125; Victoreen) additionally equipped with a count integrator, through a 5mm aperture in a lead screen. The remaining radioactivity (% of input) is plotted on a logarithmic scale against wash temperature.

For hybridization with a fluorescently-labeled probe, a volume of hybridization solution sufficient to cover the array is used, containing the probe fragment at a concentration of 2 fmoles/0.01 μl. The hybridization incubated for 5.0 hour at 17° C. and then washed at 0° C., also in hybridization buffer. Hybridized signal is observed and photographed with a fluorescence microscope (e.g. Leitz "Aristoplan"; input filter 510–560 nm, output filter 580 nm) equipped with a photocamera Using 250 ASA film, an exposure of approximately 3 minutes is taken.

For SBH, one suitable immobilization support is a 30 em-thick polyacrylamide gel covalently attached to glass. Oligonucleotides to be used as probes in this procedure are chemically synthesized (e.g. by the solid-support phosphoramidite method, deprotected in ammonium hydroxide for 12 h at 55° C. and purified by PAGE under denaturing conditions). Prior to use, primers are labeled either at the 5'-end with [γ-$^{32}$P]ATP, using T4 polynucleotide kinase, to a specific activity of about 1000 cpm/fmol, or at the 3'-end with a fluorescent label, e.g. tetramethylrhodamine (TMR), coupled to dUTP through the base by terminal transferase (Aleksandrova et al., 1990, *Molek. Biologia* [*Moscow*], 24:1100–1108) and further purified by PAGE.

An alternative method of sequencing involves subsequent rounds of stepwise ligation and cleavage of a labeled probe to a target polynucleotide whose sequence is to be determined (Brenner, U.S. Pat. No. 5,599,675). According to this method, the nucleic acid to be sequenced is prepared as a double-stranded DNA molecule with a "sticky end", in other words, a single-stranded terminal overhang, which overhang is of a known length that is uniform among the molecules of the preparation, typically 4 to 6 bases. These molecules are then probed in order to determine the identity of a particular base present in the single-stranded region, typically the terminal base. A probe of use in this method is a double-stranded polynucleotide which (i) contains a recognition site for a nuclease, and (ii) typically has a protruding strand capable of forming a duplex with a complementary protruding strand of the target polynucleotide. In each sequencing cycle, only those probes whose protruding strands form perfectly-matched duplexes with the protruding strand of the target polynucleotide hybridize- and are then ligated to the end of the target polynucleotide. The probe molecules are divided into four populations, wherein each such population comprises one of the four possible nucleotides at the position to be determined, each labeled with a distinct fluorescent dye. The remaining positions of the duplex-forming region are occupied with randomized, unlabeled bases, so that every possible multimer the length of that region is represented; therefore, a certain percentage of probe molecules in each pool are complementary to the single-stranded region of the target polynucleotide; however, only one pool bears labeled probe molecules that will hybridize.

After removal of the unligated probe, a nuclease recognizing the probe cuts the ligated complex at a site one or more nucleotides from the ligation site along the target polynucleotide leaving an end, usually a protruding strand, capable of participating in the next cycle of ligation and cleavage. An important feature of the nuclease is that its recognition site be separate from its cleavage site. In the course of such cycles of ligation and cleavage, the terminal nucleotides of the target polynucleotide are identified. As stated above, one such category of enzyme is that of type IIs restriction enzymes, which cleave sites up to 20 base pairs remote from their recognition sites; it is contemplated that such enzymes may exist which cleave at distances of up to 30 base pairs from their recognition sites.

Ideally, it is the terminal base whose identity is being determined (in which it is the base closest to the double-stranded region of the probe which is labeled), and only this base is cleaved away by the type IIs enzyme. The cleaved probe molecules are recovered (e.g. by hybridization to a complementary sequence immobilized on a bead or other support matrix) and their fluorescent emission spectrum measured using a fluorimeter or other light-gathering device. Note that fluorimetric may be made prior to cleavage of the probe from the test molecule; however, cleavage prior to qualitative analysis of fluorescence allows the next round of sequencing to commence while determination of the identity of the first sequenced base is in progress. Detection prior to cleavage is preferred where sequencing is carried out in parallel on a plurality of sequences (either segments of a single target polynucleotide or a plurality of altogether different target polynucleotides), e.g. attached to separate magnetic beads, or other types of solid phase supports, such as the replicable arrays of the invention. Note that whenever natural protein endonucleases are employed as the nuclease, the method further includes a step of methylating the target polynucleotide at the start of a sequencing operation to prevent spurious cleavages at internal recognition sites fortuitously located in the target polynucleotide.

By this method, there is no requirement for the electrophoretic separation of closely-sized DNA fragments, for difficult-to-automate gel-based separations, the generation of nested deletions of the target polynucleotide. In addition, detection and analysis are greatly simplified because signal-to noise ratios are much more favorable on a nucleotide-by-nucleotide basis, permitting smaller sample sizes to be employed. For fluorescent-based detection schemes, analysis is further simplified because fluorophores labeling different nucleotides may be separately detected in homogeneous solutions rather than in spatially overlapping bands.

As alluded to, the target polynucleotide may be anchored to a solid-phase support, such as a magnetic particle, polymeric microsphere, filter material, or the like, which permits the sequential application of reagents without complicated and time-consuming purification steps. The length of the target polynucleotide can vary widely; however, for convenience of preparation, lengths employed in conventional sequencing are preferred. For example, lengths in the range of a few hundred basepairs, 200–300, to 1 to 2 kilobase pairs are most often used.

Probes of use in the procedure may be labeled in a variety of ways, including the direct or indirect attachment of radioactive moieties, fluorescent moieties, colorimetric moieties, and the like. Many comprehensive reviews of methodologies for labeling DNA and constructing DNA probes provide guidance applicable to constructing probes (see Matthews et al., 1988, *Anal. Biochem.*, 169:1–25; Haugland, 1992, *Handbook of Fluorescent Probes and Research Chemicals*, Molecular Probes, Inc., Eugene, Oreg.; Keller and Manak, 1993, *DNA Probes*, 2nd Ed., Stockton Press, New York; Eckstein, ed., 1991, *Oligonucleotides and Analogues: A Practical Approach*, ML Press, Oxford, 1991); Wetmur, 1991, *Critical Reviews in Biochemistry and Molecular Biology*, 26:227–259). Many more particular labelling methodologies are known in the art (see Connolly, 1987, *Nucleic Acids Res.*, 15:3131–3139; Gibson et al. 1987, *Nucleic Acids Res.*, 15:5455–6467; Spoat et al., 1987, *Nucleic Acids Res.*, 15:4837–4848; Fung et al., U.S. Pat. No. 4,757,141; Hobbs, et al., U.S. Pat. No. 5,151,507; Cruickshank, U.S. Pat. No. 5,091,519; [synthesis of functionatlized oligonucleotides for attachment of reporter groups]; Jablonski et al., 1986, *Nucleic Acids Res.*, 14:6115–6128 [enzyme/oligonucleotide conjugates]; and Urdea et al., U.S. Pat. No. 5,124,246 [branched DNA]). The choice of attachment sites of labeling moieties does not significantly affect the ability of a given labeled probe to identify nucleotides in the target polynucleotide, provide that such labels do not interfere with the ligation and cleavage steps. In particular, dyes may be conveniently attached to the end of the probe distal to the target polynucleotide on either the 3' or 5' termini of strands making up the probe, e.g. Eckstein (cited above), Fung (cited above), and the like. In some cases, attaching labeling moieties to interior bases or inter-nucleoside linkages may be desirable.

As stated above, four sets of mixed probes are provided for addition to the target polynucleotide, where each is labeled with a distinguishable label. Typically, the probes are labeled with one or more fluorescent dyes, e.g. as disclosed by Menchen et al, U.S. Pat No. 5,188,934; Begot et al PCT application PCT/US90/ 05565. Each of four spectrally resolvable fluorescent labels may be attached, for example, by way of Aminolinker II (all available from Applied Biosystems, Inc., Foster City, Calif.); these include TAMRA (tetramethylrhodamine), FAM (fluorescein), ROX (rhodamine X), and JOE (2', 7'-dimethoxy-4',5'-dichlorofluorescein) and their attachment to oligonucleotides is described in Fung et al., U.S. Pat. No. 4,855,225.

Typically, nucleases employed in the invention are natural protein endonucleases (i) whose recognition site is separate from its cleavage site and (ii) whose cleavage results in a protruding strand on the target polynucleotide. Class IIS restriction endonucleases that may be employed are as previously described (Szybalski et al., 1991, Me, 100:13–26; Roberts et al., 1993, *Nucleic Acids Res.,* 21:3125–3137; Livak and Brenner, U.S. Pat No. 5,093,245). Exemplary class IIs nucleases include AlwXI, BsmAI, BbvI, BsmFI, SisI, HgaI, BscAI, BbvII, BcefI, Bce85I, BccI, BcgI, BsaI, BsgI, BspMI, Bst71 I, EarI, Eco57I, Esp3I, FauI, FokI, GsuI, HphI, MboII, MmeI, RleAI, SapI, SfaNI, TaqII, Tth111IIR, Bco5I, BpuAI, FinI, BsrDI, and isoschizomers thereof. Preferred nucleases include Fok1, HgaI, EarI, and SfaNI. Reactions are generally carried out in 50 µL volumes of manufacturer's (New England Biolabs) recommended buffers for the enzymes employed, unless otherwise indicated. Standard buffers are also described in Sambrook et al., 1989, supra.

When conventional ligases are employed, the 5' end of the probe may be phosphorylated. A 5' monophosphate can be attached to a second oligonucleotide either chemically or enzymatically with a kinase (see Sambrook et al., 1989, supra). Chemical phosphorylation is described by Horn and Urdea, 1986, *Tetrahedron Lett.,* 27:4705, and reagents for carrying out the disclosed protocols are commercially available (e.g. 51 Phosphate-ONTm from Clontech Laboratories; Palo Alto, Calif.).

Chemical ligation methods are well known in the art, e.g. Ferris et al., 1989, *Nucleosides & Nucleotides,* 8:407–414; Shabarova et al., 1991, *Nucleic Acids Res.,* 19:4247–4251. Typically, ligation is carried out enzymatically using a ligase in a standard protocol. Many ligases are known and are suitable for use in the invention (Lehman, 1974, *Science* 186:790–797; Engler et al., 1982, "DNA Ligases", in Boyer, ed., *The Enzymes, Vol.* 15B pp. 3–30, Academic Press, New York). Preferred ligases include T4 DNA ligase, T7 DNA ligase, *E. coli* DNA ligase, Taq ligase, Pfu ligase and Tth ligase. Protocols for their use are well known, (e.g. Sambrook et al., 1989, supra; Barany, 1991, *PCR Methods and Applications,* 1:5–16; Marsh et al., 1992, *Strategies,* 5:73–76). Generally, ligases require that a 5' phosphate group be present for ligation to the 3'hydroxyl of an abutting strand. This is conveniently provided for at least one strand of the target polynucleotide by selecting a nuclease which leaves a 5' phosphate, e.g. FokI.

Prior to nuclease cleavage steps, usually at the start of a sequencing operation, the target polynucleotide is treated to block the recognition sites and/or cleavage sites of the nuclease being employed. This prevents undesired cleavage of the target polynucleotide because of the fortuitous occurrence of nuclease recognition sites at interior locations in the target polynucleotide. Blocking can be achieved in a variety of ways, including methylation and treatment by sequence-specific aptamers, DNA binding proteins, or oligonucleotides that form triplexes. Whenever natural protein endonucleases are employed, recognition sites can be conveniently blocked by methylating the target polynucleotide with the so-called "cognate" methylase of the nuclease being used; for most (if not all) type II bacterial restriction endonucleases, there exist cognate methylases that methylate their corresponding recognition sites. Many such methylases are known in the art (Roberts et al., 1993, supra; Nelson et al., 1993, *Nucleic Acids Res.,* 21:3139–3154) and are commercially available from a variety of sources, particularly New England Biolabs (Beverly, Mass.).

The method includes an optional capping step after the unligated probe is washed from the target polynucleotide. In a capping step, by analogy with polynucleotide synthesis (e.g. Andrus et al., U.S. Pat. No. 4,816,571), target polynucleotides that have not undergone ligation to a probe are rendered inert to further ligation steps in subsequent cycles. In this manner spurious signals from "out of phase" cleavages are prevented. When a nuclease leaves a 5' protruding strand on the target polynucleotides, capping is usually accomplished by exposing the c unreacted target polynucleotides to a mixture of the four dideoxynucleoside triphosphates, or other chain-terminating nucleoside triphosphates, and a DNA polymerase. The DNA polymerase extends the Y strand of the unreacted target polynucleotide by one chain-terminating nucleotide, e.g. a dideoxynucleotide, thereby rendering it incapable of ligating with probe in subsequent cycles.

Alternatively, a simple method involving quantitative incremental fluorescent nucleotide addition sequencing (QIFNAS), is employed in which each end of each clonal oligonucleotide is sequenced by primer extension with a nucleic acid polymerase (e.g. Klenow or Sequenase™; U.S. Biochemicals) and one nucleotide at a time which has a traceable level of the corresponding fluorescent dNTP or rNTP, for example, 100 micromolar dCTP and 1 micromolar fluorescein-dCTP. This is done sequentially, e.g. dATP, dCTP, dGTP, dTTP, dATP and so forth until the incremental change in fluorescence is below a percentage that is adequate for useful discrimination from the cumulative total from previous cycles. The length of the sequence so determined may be extended by any of periodic photobleaching or cleavage of the accumulated fluorescent label from nascent nucleic acid molecules or denaturing the nascent nucleic acid strands from the array and re-priming the synthesis using sequence already obtained.

After features are identified on a first array of the set, it is desirable to provide landmarks by which subsequently-produced arrays of the set are aligned with it, thereby enabling workers to locate on them features of interest. This is important, as the first array of a set produced by the method of the invention is, by nature, random, in that the nucleic acid molecules of the starting pool are not placed down in a specific or pre-ordered pattern based upon knowledge of their sequences.

Several types of markings are made according to the technology available in the art. For instance, selected features are removed by laser ablation (Matsuda and Chung 1994, *ASAIO Journal,* 40(3):M594–7; Jay, 1988, *Proc. Natl. Acad. Sci. U.S.A.,* 85:5454–5458; Kimble, 1981, *Dev. Biol.,* 87(2):286–300) or selectively replicated on copies of an array by laser-enhanced adhesion (Emmert-Buck et al, 1996, *Science,* 274(5289):998–1001). These methods are used to eliminate nucleic acid features that interfere with adjacent features or to create a pattern that is easier for software to align.

Laser ablation is carried out as follows: A KrF excimer laser, e.g. a Hamamatsu L4500 (Hamamatsu, Japan) (pulse wavelength, 248 nm; pulse width, 20 ns) is used as the light source. The laser beam is converged through a laser-grade UV quartz condenser lens to yield maximum fluences of 3.08 $J/cm^2$ per pulse. Ablation of the matrix and underlying glass surface is achieved by this method. The depth of etching into the glass surfaces is determined using real-time scanning laser microscopy (Lasertec 1LM21W, Yokohama, Japan), and a depth profile is determined.

Selective transfer of features via laser-capture microdissection proceeds as follows: A flat film (100 µm thick) is made by spreading a molten thermoplastic material e.g. ethylene vinyl acetate polymer (EVA; Adhesive Technologies; Hampton, N.H.) on a smooth silicone or polytetrafluoroethylene surface. The optically-transparent thin film is placed on top of an array of the invention, and the array/film sandwich is viewed in an inverted microscope (e.g. and Olympus Model CK2; Tokyo) at 100× magnification (10× objective). A pulsed carbon dioxide laser beam is introduced by way of a small front-surface mirror coaxial with the condenser optical path, so as to irradiate the upper surface of the EVA film. The carbon dioxide laser (either Apollo Company model 580, Los Angeles, or California Laser Company model LS150, San Marcos, Calif.) provides individual energy pulses of adjustable length and power. A ZnSe lens focuses the laser beam to a target of adjustable spot size on the array. For transfer spots of 150 μm diameter, a 600-microsecond pulse delivers 25–30 mW to the film. The power is decreased or increased approximately in proportion to the diameter of the laser spot focused on the array. The absorption coefficient of the EVA film, measured by Fourier transmission, is 200 cm$^{-1}$ at a laser wavelength of 10.6 μm. Because >90% of the laser radiation is absorbed within the thermoplastic film, little direct heating occurs. The glass plate or chip upon which the semi-solid support has been deposited provides a heat sink that confines the full-thickness transient focal melting of the thermoplastic material to the targeted region of the array. The focally-molten plastic moistens the targeted tissue. After cooling and recrystallization, the film forms a local surface bond to the targeted nucleic acid molecules that is stronger than the adhesion forces that mediate their affinity for the semi-solid support medium. The film and targeted nucleic acids are removed from the array, resulting in focal microtransfer of the targeted nucleic acids to the film surface.

If removal of molecules from the array by this method is performed for the purpose of ablation, the procedure is complete. If desired, these molecules instead are amplified and cloned out, as described in Example 7.

A method provided by the invention for the easy orientation of the nucleic acid molecules of a set of arrays relative to one another is "array templating". A homogeneous solution of an initial library of single-stranded DNA molecules is spread over a photolithographic all-10-mer ss-DNA oligomer array under conditions which allow sequences comprised by library members to become hybridized to member molecules of the array, forming an arrayed library where the coordinates are in order of sequence as defined by the array. For example, a 3'-immobilized 10-mer (upper strand), binds a 25-mer library member (lower strand) as shown below:

5'-TGCATGCTAT-3' [SEQ ID NO: 2]

3'-CGATGCATTTACGTAACGTACGATA-5' [SEQ ID NO: 3]

Covalent linkage of the 25-mer sequence to the support, amplification and replica printing are performed by any of the methods described above. Further characterization, if required, is carried out by SBH, fluorescent dNTP extension or any other sequencing method applicable to nucleic acid arrays, such as are known in the art. This greatly enhances the ability to identify the sequence of a sufficient number of oligomer features in the replicated array to make the array useful in subsequent applications.

EXAMPLE 2

Ordered chromosomal arrays according to the invention

Direct in situ single-copy (DISC)-PCR is a method that uses two primers that define unique sequences for on-slide PCR directly on metaphase chromosomes (Troyer et al., 1994a, *Mammalian Genome,* 5:112–114; summarized by Troyer et al., 1997, *Methods Mol Biol., Vol.* 71: *PRINS and In Situ PCR Protocols,* J. R. Godsen, ed., Humana Press, Inc., Totowa, N.J., pp. 71–76). It thus allows exponential accumulation of PCR product at specific sites, and so may be adapted for use according to the invention.

The DISC-PCR procedure has been used to localize sequences as short as 100–300 bp to mammalian chromosomes (Troyer et al., 1994a, supra; Troyer et al., 1994b, *Cytogenet. Cell Genetics,* 67(3), 199–204; Troyer et al., 1995, *Anim. Biotechnology,* 6(1):51–58; and Xie et al., 1995, *Mammalian Genome* 6:139–141). It is particularly suited for physically assigning sequence tagged sites (STSs), such as microsatellites (Litt and Luty, 1989, *Am. J. Hum. Genet,* 44:397–401; Weber and May, 1989, *Am. J. Hum. Genet* 44, 338–396), many of which cannot be assigned by in situ hybridization because they have been isolated from small-insert libraries for rapid sequencing. It can also be utilized to map expressed sequence tags (ESTs) physically (Troyer, 1994a, supra; Schmutz et al., 1996, *Cytogenet. Cell Genetics,* 72:37–39). DISC-PCR obviates the necessity for an investigator to have a cloned gene in hand, since all that is necessary is to have enough sequence information to synthesize PCR primers. By the methods of the invention, target-specific primers need not even be utilized; all that is required is a mixed pool of primers whose members have at one end a 'universal' sequence, suitable for manipulations such as restriction endonuclease cleavage or hybridization to oligonucleotide molecules immobilized on- or added to a semi-solid support and, at the other end, an assortment of random sequences (for example, every possible hexamer) which will prime in situ amplification of the chromosome. As described above, the primers may include terminal crosslinking groups with which they may be attached to the semi-solid support of the array following transfer; alternatively, they may lack such an element, and be immobilized to the support either through ultraviolet crosslinking or through hybridization to complementary, immobilized primers and subsequent primer extension, such that the newly-synthesized strand becomes permanently bound to the array. The DISC-PCR procedure is summarized briefly as follows:

Metaphase chromosomes anchored to glass slides are prepared by standard techniques (Halnan, 1989, *in Cytogenetics of Animals,* C. R. E. Halnan, ed., CAB International, Wallingford, U.K., pp. 451–456; ), using slides that have been pre-rinsed in ethanol and dried using lint-free gauze. Slides bearing chromosome spreads are washed in phosphate-buffered saline (PBS; 8.0 g NaCl, 1.3 g NaHPO$_4$ and 4 g NaH$_2$PO$_4$ dissolved in deionized water, adjusted to a volume of 1 liter and pH of 7.4) for 10 min and dehydrated through an ethanol series (70-, 80-, 95-, and 100%). Note that in some cases, overnight fixation of chromosomes in neutral-buffered formalin followed by digestion for 15 minutes with pepsinogen (2 mg/ml; Sigma) improves amplification efficiency.

For each slide, the following solution is prepared in a microfuge tube: 200 μM each dATP, dCTP, dGTP and dTTP; all deoxynucleotides are maintained as frozen, buffered 10 mM stock solutions or in dry form, and may be obtained either in dry or in solution from numerous suppliers (e.g. Perkin Elmer, Norwalk, Conn.; Sigma, St. Louis, Mo.; Pharmacia, Uppsala, Sweden). The reaction mixture for each slide includes 1.5 μM each primer (from 20 μM stocks), 2.0 μL 10× Taq polymerase buffer (100 mM Tris-HCl, pH 8.3, 500 mM KCl, 15 mM MgCl$_2$, 0.1% BSA; Perkin Elmer), 2.5 units AmpliTaq polymerase (Perkin Elmer) and deionzed H$_2$O to a final volume of 20 pl. Note that the commercially supplied Taq polymerase buffer is normally adequate; however, adjustments may be made as needed in [MgCl$_2$] or pH, in which case an optimization kit, such as the Opti-Primer PCR Kit (Stratagene; La Jolla, Calif.) may be used. The above reaction mixture is pipetted onto the metaphase chromosomes and covered with a 22×50 mm coverslip, the perimeter of which is then sealed with clear nail polish. All air bubbles, even the smallest, are removed prior to sealing, as they expand when heated, and will inhibit the reaction. A particularly preferred polish is Hard As Nails (Sally Hansen); this nail enamel has been found to be resistant to leakage, which, if it occurred, would also compromise the integrity of the reaction conditions and inhibit amplification of the chromosomal DNA sequences. One heavy coat is sufficient. After the polish has been allowed to dry at room temperature, the edges of the slide are covered with silicone grease (Dow Coming Corporation, Midland, Mich.). Slides are processed in a suitable thermal cycler (i.e. one designed for on-slide PCR, such as the BioOven III; Biotherm Corp., Fairfax, Va.) using the following profile:

a. 94° C. for 3 min.

b. Annealing temperature of primers for 1 min.

c. 72° C. for 1 min.

d. 92° C. for 1 min.

e. Cycle to step b 24 more times (25 cycles total).

f. Final extension step of 3–5 min.

After thermal cycling is complete, silicone grease is removed with a tissue, and the slide is immersed in 100% ethanol. Using a sharp razor blade, the nail polish is cut through and the edge of the coverslip is lifted gently and removed. It is critical that the slide never be allowed to dry from this point on, although excess buffer is blotted gently off of the slide edge. The slide is immersed quickly in 4×SSC and excess nail polish is scraped from the edges of the slide prior to subsequent use.

The slide is contacted immediately with a semi-solid support in order to transfer to it the amplified nucleic acid molecules; alternatively, that the slide is first equilibrated in a liquid medium that is isotonic with- or, ideally, identical to that which permeates (i.e. is present in the pores of-) the semi-solid support matrix. From that point on, the array is handled comparably with those prepared according to the methods presented in Example 1. Feature identification, also as described above, permits determination of the approximate positions of genetic elements along the length of the template chromosome. In preparations in which chromosomes are linearly extended (stretched), the accuracy of gene ordering is enhanced. This is particularly useful in instances in which such information is not known, either through classical or molecular genetic studies, even in the extreme case of a chromosome that is entirely uncharacterized. By this method, comparative studies of homologous chromosomes between species of interest are performed, even if no previous genetic mapping has been performed on either. The information so gained is valuable in terms of gauging the evolutionary relationships between species, in that both large and small chromosomal rearrangements are revealed. The genetic basis of phenotypic differences between different individuals of a single species, e.g. human subjects, is also investigated by this method. When template chromosomes are condensed (coiled), more information is gained regarding the in vivo spatial relationships among genetic elements. This may have implications in terms of cell-type specific gene transcriptional activity, upon which comparison of arrays generated from samples comprising condensed chromosomes drawn from cells of different tissues of the same organism may shed light.

While the methods by which histological samples are prepared, PCR is performed and the first copy of the chromosomal array is generated are time-consuming, multiple copies of the array are produced easily according to the invention, as described above in Example 1 and elsewhere. The ability of the invention to reproduce what would, otherwise, be a unique array provides a valuable tool by which scientists have the power to work in parallel- or perform analyses of different types upon comparable samples. In addition, it allows for the generation of still more copies of the array for distribution to any number of other workers who may desire to confirm or extend any data set derived from such an array at any time.

A variation on this use of the present invention is chromosome templating. DNA (e.g. that of a whole chromosome) is stretched out and fixed on a surface (Zimmermann and Cox, 1994, *Nucleic Acids Res.*, 22(3) :492–497). Segments of such immobilized DNA are made single-stranded by exonucleases, chemical denaturants (e.g. formamide) and/or heat. The single stranded regions are hybridized to the variable portions of an array of single-stranded DNA molecules each bearing regions of randomized sequence, thereby forming an array where the coordinates of features correspond to their order on a linear extended chromosome. Alternatively, a less extended structure, which replicates the folded or partially-unfolded state of various nucleic acid compartments in a cell, is made by using a condensed (coiled), rather than stretched, chromosome.

EXAMPLE 3

RNA localization arrays

The methods described in Example 2, above, are applied with equal success to the generation of an array that provides a two-dimensional representation of the spatial distribution of the RNA molecules of a cell. This method is applied to 'squashed' cellular material, prepared as per the chromosomal spreads described above in Example 2; alternatively, sectioned tissue samples affixed to glass surfaces are used. Either paraffin-, plastic- or frozen (Serrano et al., 1989, *Dev. Biol.* 132:410–418) sections are used in the latter case.

Tissue samples are fixed using conventional reagents; formalin, 4% paraformaldehyde in an isotonic buffer, formaldehyde (each of which confers a measure of RNAase resistance to the nucleic acid molecules of the sample) or a multi-component fixative, such as FAAG (85% ethanol 4% formaldehyde, 5% acetic acid, 1% EM grade glutaraldehyde) is adequate for this procedure. Note that water used in the preparation of any aqueous components of solutions to which the tissue is exposed until it is embedded is RNAase-free, i.e. treated with 0.1% diethylprocarbonate (DEPC) at room temperature overnight and subsequently autoclaved for 1.5 to 2 hours. Tissue is fixed at 4° C., either on a sample roller or a rocking platform, for 12 to 48 hours in order to allow fixative to reach the center of the sample. Prior to embedding, samples are purged of fixative and dehydrated; this is accomplished through a series of two- to ten-minute washes in increasingly high concentrations of ethanol, beginning at 60%- and ending with two washes in 95%/- and another two in 100% ethanol, followed two ten-minute washes in xylene. Samples are embedded in any of a variety of sectioning supports, e.g. paraffin, plastic polymers or a mixed paraffin/polymer medium (e.g. Paraplast®Plus Tissue Embedding Medium, supplied by Oxford Labware). For example, fixed, dehydrated tissue is transferred from the second xylene wash to paraffin or a paraffin/polymer resin in the liquid-phase at about 58 ° C., then replace three to six times over a period of approximately three hours to dilute out residual xylene, followed by overnight incubation at 58° C. under a vacuum, in order to optimize infiltration of the embedding medium in to the tissue. The next day, following several more changes of medium at 20 minute to one hour intervals, also at 58° C., the tissue sample is positioned in a sectioning mold, the mold is surrounded by ice water and the medium is allowed to harden. Sections of 6 µm thickness are taken and affixed to 'subbed' slides, which are those coated with a proteinaceous substrate material, usually bovine serum albumin (BSA), to promote adhesion. Other methods of fixation and embedding are also applicable for use according to the methods of the invention; examples of these are found in Humason, G. L., 1979, *Animal Tissue Techniques,* 4th ed. (W. H. Freeman & Co., San Francisco), as is frozen sectioning.

Following preparation of either squashed or sectioned tissue, the RNA molecules of the sample are reverse-transcribed in situ. In order to contain the reaction on the slide, tissue sections are placed on a slide thermal cycler (e.g. Tempcycler II; COY Corp., Grass Lake, Mich.) with heating blocks designed to accommodate glass microscope slides. Stainless steel or glass (Bellco Glass Inc.; Vineland, N.J.) tissue culture cloning rings approximately 0.8 cm (inner diameter)×1.0 cm in height are placed on top of the tissue section. Clear nail polish is used to seal the bottom of the ring to the tissue section, forming a vessel for the reverse transcription and subsequent localized in situ amplification (LISA) reaction (Tsongalis et al., 1994, supra).

Reverse transcription is carried out using reverse transcriptase, (e.g. avian myoblastosis virus reverse transcriptase, AMV-RT; Life Technologies/Gibco-BRL or Moloney Murine Leukemia Virus reverse transcriptase, M-MLV-RT, New England Biolabs, Beverly, Mass.) under the manufacturer's recommended reaction conditions. For example, the tissue sample is rehydrated in the reverse transcription reaction mix, minus enzyme, which contains 50 mM Tris.HCl (pH 8.3), 8 mM $MgCl_2$, 10 mM dithiothreitol, 1.0 mM each dATP, dTTP, dCTP and dGTP and 0.4 mM oligo-dT (12- to 18-mers). The tissue sample is, optionally, rehydrated in RNAase-free TE (10 mM Tris.HCl, pH 8.3 and 1 mM EDTA), then drained thoroughly prior to a addition of the reaction buffer. To denature the RNA molecules, which may have formed some double-stranded secondary structures, and to facilitate primer annealing, the slide is heated to 65° C. for 1 minute, after which it is cooled rapidly to 37° C. After 2 minutes, 500 units of M-MLV-RT are added the mixture, bringing the total reaction volume to 100 µl. The reaction is incubated at 37° C. for one hour, with the reaction vessel covered by a microscope cover slip to prevent evaporation.

Following reverse transcription, reagents are pipetted out of the containment ring structure, which is rinsed thoroughly with TE buffer in preparation for amplification of the resulting cDNA molecules.

The amplification reaction is performed in a total volume of 25 µl, which consists of 75 ng of both the forward and reverse primers (for example the mixed primer pools I and 2 of Example 6) and 0.6 U of Taq polymerase in a reaction solution containing, per liter: 200 nmol of each deoxynucleotide triphosphate, 1.5 mmol of $MgCl_2$, 67 mmol of Tris.HCl (pH 8.8), 10 mmol of 2-mercaptoethanol, 16.6 mmol of ammonium sulfate, 6.7 µmol of EDTA, and 10 µmol of digoxigenin-11-dUTP. The reaction mixture is added to the center of the cloning ring, and layered over with mineral oil to prevent evaporation before slides are placed back onto the slide thermal cycler. DNA is denatured in situ at 94° C. for 2 min prior to amplification. LISA is accomplished by using 20 cycles, each consisting of a 1-minute primer annealing step (55° C.), a 1.5-min extension step (72° C.), and a 1-min denaturation step (94° C.). These amplification cycle profiles differ from those used in tube amplification to preserve optimal tissue morphology, hence the distribution of reverse transcripts and the products of their amplification on the slide.

Following amplification, the oil layer and reaction mix are removed from the tissue sample, which is then rinsed with xylene. The containment ring is removed with acetone, and the tissue containing the amplified cDNA is rehydrated by washing three times in approximately 0.5 ml of a buffer containing 100 mM Tris-Cl (pH 7.5) and 150 mM NaCl. The immobilized nucleic acid array of the invention is then formed by contacting the amplified nucleic acid molecules with a semi-solid support and covalently crosslinking them to it, by any of the methods described above.

Features are identified using SBH, also as described above, and correlated with the positions of mRNA molecules in the cell.

EXAMPLE 4

Size-sorted genomic arrays

As mentioned above, it is possible to prepare a support matrix in which are embedded whole, even living, cells. Such protocols have been developed for various purposes, such as (encapsulated, implantable cell-based drug-delivery vehicles—check to see what they're called), (purpose listed above with protocol citation) and the delivery to an electophoresis matrix of very large, unsheared DNA molecules, as required for pulsed-field gel electrophoresis (Schwartz and Cantor, 1984, *Cell,* 37:67–75). The arrays of the invention are constructed using as the starting material genomic DNA from a cell of an organism that has been embedded in an electrophoretic matrix and lysed in situ, such that intact nucleic acid molecules are released into the support matrix environment. If an array based upon copies of large molecules is made, such as is of use in a fashion similar to the chromosomal element ordering arrays described above in Example 2, then a low-percentage agarose gel is used as a support. Following lysis (what method—need pulsed-field reference), the resulting large molecules may be size-sorted electrophoretically prior to in situ PCR amplification and linkage to the support, both as described above. If it is desired to preserve the array on a support other than agarose, which may be difficult to handle if the gel is large, the array is transferred via electroblotting onto a second support, such as a nylon or nitrocellulose membrane prior to linkage.

If it is not considered essential to preserve the associations between members of genetic linkage groups (at the coarsest level of resolution, chromosomes), nucleic acid molecules are cleaved, mechanically, chemically or enzymatically, prior to electrophoresis. A more even distribution of nucleic acid over the support results, and physical separation of individual elements from one another is improved. In such a case, a polyacrylamide, rather than agarose, gel matrix is used as a support. The arrays produced by this method do, to a certain extent, resemble sequencing gels; cleavage of an electrophoresed array, e.g. with a second restriction enzyme or combination thereof, followed by electrophoresis in a second dimension improves resolution of individual nucleic acid sequences from one another.

Such an array is constructed to any desired size. It is now feasible to scan large gels (for example, 40 cm in length) at high resolution. In addition, advances in gel technology now permit sequencing to be performed on gels a mere 4 cm long, one tenth the usual length, which demonstrates that a small gel is also useful according to the invention.

EXAMPLE 5

Spray-painted arrays (inkjet)

Immobilized nucleic acid molecules may, if desired, be produced using a device (e.g., any commercially-available inkjet printer, which may be used in substantially unmodified form) which sprays a focused burst of nucleic acid synthesis compounds onto a support (see Castellino, 1997, *Genome Res.*, 7:943–976). Such a method is currently in practice at Incyte Pharmaceuticals and Rosetta Biosystems, Inc., the latter of which employs what are said to be minimally-modified Epson inkjet cartridges (Epson America, Inc.; Torrance, Calif.). The method of inkjet deposition depends upon the piezoelectric effect, whereby a narrow tube containing a liquid of interest (in this case, oligonucleotide synthesis reagents) is encircled by an adapter. An electric charge sent across the adapter causes the adapter to expand at a different rate than the tube, and forces a small drop of liquid containing phosphoramidite chemistry reagents from the tube onto a coated slide or other support.

Reagents are deposited onto a discrete region of the support, such that each region forms a feature of the array; the desired nucleic acid sequence is synthesized drop-by-drop at each position, as is true in other methods known in the art. If the angle of dispersion of reagents is narrow, it is possible to create an array comprising many features. Alternatively, if the spraying device is more broadly focused, such that it disperses nucleic acid synthesis reagents in a wider angle, as much as an entire support is covered each time, and an array is produced in which each member has the same sequence (i.e. the array has only a single feature).

Arrays of both types are of use in the invention; a multi-feature array produced by the inkjet method is used in array templating, as described above; a random library of nucleic acid molecules are spread upon such an array as a homogeneous solution comprising a mixed pool of nucleic acid molecules, by contacting the array with a tissue sample comprising nucleic acid molecules, or by contacting the array with another array, such as a chromosomal array (Example 2) or an RNA localization array (Example 3).

Alternatively, a single-feature array produced by the inkjet method is used by the same methods to immobilize nucleic acid molecules of a library which comprise a common sequence, whether a naturally-occurring sequence of interest (e.g. a regulatory motif) or an oligonucleotide primer sequence comprised by all or a subset of library members, as described herein above and in Example 6, below.

Nucleic acid molecules which thereby are immobilized upon an ordered inkjet array (whether such an array comprises one or a plurality of oligonucleotide features) are amplified in situ, transferred to a semi-solid support and immobilized thereon to form a first randomly-patterned, immobilized nucleic acid array, which is subsequently used as a template with which to produce a set of such arrays according to the invention, all as described above.

EXAMPLE 6

Isolation of a feature from an array of the invention (Method 1)/Heterologous arrays As described above in Example 1, sets of arrays are, if desired, produced according to the invention such that they incorporate oligonucleotide sequences bearing restriction sites linked to the ends of each feature. This provides a method for creating spatially-unique arrays of primer pairs for in situ amplification, in which each feature has a distinct set of primer pairs. One or both of the universal primers comprises a restriction endonuclease recognition site, such as a type sequence (e.g. as Eco571 or MmeI which will cut up to 20 bp away). Treatment of the whole double-stranded array with the corresponding enzyme(s) followed by melting and washing away the non-immobilized strand creates the desired primer pairs with well-defined 3' ends. Alternatively, a double-strand-specific 3' exonuclease treatment of the double-stranded array is employed, but the resulting single-stranded 3' ends may vary in exact endpoint. The 3' end of the primers are used for in situ amplification, for example of variant sequences in diagnostics. This method, by which arrays of unique primer pairs are produced efficiently, provides an advance over the method of Adams and Kron (1997, supra), in which each single pair of primers is manually constructed and placed. Cloning of a given feature from an array of such a set is performed as follows:

MmeI is a restriction endonuclease having the property of cleaving at a site remote from its recognition site, TCCGAC. Heterogeneous pools of primers are constructed that comprise (from 5' to 3') a sequence shared by all members of the pool, the MmeI recognition site, and a variable region. The variable region may comprise either a fully-randomized sequence (e.g. all possible hexamers) or a selected pool of sequences (e.g. variations on a particular protein-binding, or other, functional sequence motif). If the variable sequence is random, the length of the randomized sequence determines the sequence complexity of the pool. For example, randomization of a hexameric sequence at the 3' ends of the primers results in a pool comprising 4,096 distinct sequence combinations. Examples of two such mixed populations of oligonucleotides (in this case, 32-mers) are primer pools 1s and 2s, below:

```
primer 1 (a pool of 4096 32-mers):
5'gcagcagtacgactagcataTCCGACnnnnnn3' [SEQ ID NO: 4]

primer 2 (a pool of 4096 32-mers):
5'cgatagcagtagcatgcaggTCCGACnnnnnn3' [SEQ ID NO: 5]
```

A nucleic acid preparation is amplified, using primer 1 to randomly prime synthesis of sequences present therein. The starting nucleic acid molecules are cDNA or genomic DNA, either of which may comprise molecules that are substantially whole or that are into smaller pieces. Many DNA cleavage methods are well known in the art. Mechanical cleavage is achieved by several methods, including sonication, repeated passage through a hypodermic needle, boiling or repeated rounds of rapid freezing and thawing. Chemical cleavage is achieved by means which include, but are not limited to, acid or base hydrolysis, or cleavage by base-specific cleaving substances, such as are used in DNA sequencing (Maxam and Gilbert, 1977, *Proc. Natl. Acad. Sci. U.S.A.*, 74:560–564). Alternatively, enzymatic cleavage that is site-specific, such as is mediated by restriction endonucleases, or more general, such as is mediated by exo- and endonucleases e.g. ExoIII, mung bean nuclease, DNAase I or, under specific buffer conditions, DNA polymerases (such as T4), which chew back or internally cleave DNA in a proofreading capacity, is performed. If the starting nucleic acid molecules (which may, additionally, comprise RNA) are fragmented rather than whole (whether closed circular or chromosomal), so as to have free ends to which a second sequence may be attached by means other than primed synthesis, the MmeI recognition sites may be linked to the starting molecules using DNA ligase, RNA ligase or terminal deoxynucleotide transferase. Reaction conditions for these enzymes are as recommended by the manufacturer (e.g. New England Biolabs; Beverly, Mass. or Boehringer Mannheim Biochemicals, Indianapolis, Ind.). If employed, PCR is performed using template DNA (at least 1 fg; more usefully, 1–1,000 ng) and at least 25 pmol of oligonucleotide primers; an upper limit on primer concentration is set by aggregation at about 10 µg/ml. A typical reaction mixture includes: 2 µl of DNA, 25 pmol of oligonucleotide primer, 2.5 µl of 10× PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler. The length and temperature of each step of a PCR cycle, as well as the number of cycles, is adjusted in accordance to the stringency requirements in effect. Initial denaturation of the template molecules normally occurs at between 92° C. and 99° C. for 4 minutes, followed by 20–40 cycles consisting of denaturation (94–99° C. for 15 seconds to 1 minute), annealing (temperature determined as discussed below, 1–2 minutes), and extension (72° C. for 1 minute). Final extension is generally for 4 minutes at 72° C., and may be followed by an indefinite (0–24 hour) step at 4° C.

Annealing temperature and timing are determined both by the efficiency with which a primer is expected to anneal to a template and the degree of mismatch that is to be tolerated. In attempting to amplify a mixed population of molecules, the potential loss of molecules having target sequences with low melting temperatures under stringent (high-temperature) annealing conditions against the promiscuous annealing of primers to sequences other than their target sequence is weighed. The ability to judge the limits of tolerance for feature loss vs. the inclusion of artifactual amplification products is within the knowledge of one of moderate skill in the art. An annealing temperature of between 30° C. and 65° C. is used. An example of one primer out of the pool of 4096 primer 1, one primer (primer 1 ex) is shown below, as is a DNA sequence from the preparation with which primer 1ex has high 3' end complementarity at a random position. The priming site is underlined on either nucleic acid molecule.

```
primer 1ex [SEQ ID NO: 7; bases 1-32]:   5'-gcagcagtacgactagcataTCCGAC ctgcgt-3' genomic DNA [SEQ ID NO: 6]:              3'-tttcgacgcacatcgcgtgcatggccccatgcatcagg
                                            ctgacgaccgtcgtacgtctactcggct-5'
```

After priming, polymerase extension of primer 1ex on the template results in:

```
5'-gcagcagtacgactagcataTCCGACctgcgtgtagcgcacgtaccggggtacgtagtcc[SEQ ID NO: 7]
gactgctggcagcatgcagatgagccga-3'
```

Out of the pool of 4096 primer 2, one primer with high 3' end complementarity to a random position in the extended primer 1ex DNA is selected by a polymerase for priming (priming site in bold):

```
5'-gcagcagtacgactagcataTCCGACctgcgtgtagcgcacgtaccggggtacgtagtcc  [SEQ ID NO: 7]
gactgctggcagcatgcagatgagccga 3'
``` primer 2ex [SEQ ID NO: 8; bases 1–32]:
3'-gacgacCAGCCTggacgtacgatgacgatagc-5'
After priming and synthesis, the resulting second strand is:

```
3'-cgtcgtcatgctgatcgtatAGGCTGgacgcacatcgcgtgcatggccccatgcatcagg  [SEQ ID NO: 8]
ctgacgacCAGCCTggacgtacgatgacgatagc-5'
```

Primer 3, shown below, is a 26-mer that is identical to the constant region of primer 1ex: [SEQ ID NO: 7; nucleotides 1-26] 5'-gcagcagtacgactagcataTCCGAC-3' It is immobilized by a 5' acrylyl group to a polyacrylamide layer on a glass slide.

Primer 4, below, is a 26-mer that is complementary to the constant region of primer 2ex: [SEQ ID NO: 8; nucleotides 1-26] 5'-cgatagcagtagcatgcaggTCCGAC-3' It is optionally immobilized to the polyacrylamide layer by a 5' acrylyl group.

The pool of amplified molecules derived from the sequential priming of the original nucleic acid preparation with mixed primers I and 2, including the product of 1ex/2ex priming and extension, are hybridized to immobilized primers 3 and 4. In situ PCR is performed as described above, resulting in the production of a first random, immobilized array of nucleic acid molecules according to the invention. This array is replicated by the methods described in Example 1 in order to create a plurality of such arrays according to the invention.

After in situ PCR using primers 3 and 4:

```
5'-gcagcagtacgactagcataTCCGACctgcgtgtagcgcacgtaccggggtacgtagt
3'-cgtcgtcatgctgatcgtatAGGCTGgacgcacatcgcgtgcatggccccatgcatca ccgactgctgGTCGGAcctgcatgctactgctatcg-3' [SEQ ID NO: 9]
ggctgacgacCAGCCTggacgtacgatgacgatagc-5' [SEQ ID NO: 8]
```

After cutting with MmeI and removal of the non-immobilized strands:

```
[SEQ ID NO: 9; bases 1-46]  5'-gcagcagtacgactagcataTCCGACctgcgtgtagcgcacgtacc-3'
                                (primer 1-based, clone-specific oligonucleotide)

[SEQ ID NO: 8; bases 1-46]  3'-ccatgcatcaggctgacgacCAGCCTggacgtacgatgacgatagc-5'
                                (primer 2-based, clone-specific oligonucleotide)
```

The resulting random arrays of oligonucleotide primers representing the nucleic acid sequences of the original preparation are useful in several ways. Any particular feature, such as the above pair of primers, is used selectively to amplify the intervening sequence (in this case two central bp of the original 42 bp cloned segment are captured for each use of the chip or a replica) from a second nucleic acid sample. This is performed in solution or in situ, as described above, following feature identification on the array, using free, synthetic primers. If desired, allele-specific primer extension or subsequent hybridization is performed.

Importantly, this technique provides a means of obtaining corresponding, or homologous, nucleic acid arrays from a second cell line, tissue, organism or species according to the invention. The ability to compare corresponding genetic sequences derived from different sources is useful in many experimental and clinical situations. By "corresponding genetic sequences", one means the nucleic acid content of different tissues of a single organism or tissue-culture cell lines. Such sequences are compared in order to study the cell-type specificity of gene regulation or mRNA processing or to observe chromosomal rearrangements that might arise in one tissue rather than another. Alternatively, the term refers to nucleic acid samples drawn from different individuals, in which case a given gene or its regulation is compared between or among samples. Such a comparison is of use in linkage studies designed to determine the genetic basis of disease, in forensic techniques and in population genetic studies. Lastly, it refers to the characterization and comparison of a particular nucleic acid sequence in a first organism and its homologues in one or more other organisms that are separated evolutionarily from it by varying lengths of time in order to highlight important (therefore, conserved) sequences, estimate the rate of evolution and/or establish phylogenetic relationships among species. The invention provides a method of generating a plurality of immobilized nucleic acid arrays, wherein each array of the plurality contains copies of nucleic acid molecules from a different tissue, individual organism or species of organism.

Alternatively, a first array of oligonucleotide primers with sequences unique to members of a given nucleic acid preparation is prepared by means other than the primed synthesis described above. To do this, a nucleic acid sample is obtained from a first tissue, cell line, individual or species and cloned into a plasmid or other replicable vector which comprises, on either side of the cloning site, a type IIS enzyme recognition site sufficiently close to the junction between vector and insert that cleavage with the type IIS enzyme(s) recognizing either site occurs within the insert sequences, at least 6 to 10, preferably 10 to 20, base pairs away from the junction site. It is contemplated that type IIS restriction endonuclease activity may even occur at a distance of up to 30 pairs from the junction site. The nucleic acid molecules are cleaved from the vector using restriction enzymes that cut outside of both the primer and oligonucleotide sequences, and are then immobilized on a semi-solid support according to the invention by any of the methods described above in which covalent linkage of molecules to the support occurs at their 5' termini, but does not occur at internal bases. Cleavage with the type IIS enzyme (such as MmeI) to yield the immobilized, sequence-specific oligonucleotides is performed as described above in this Example.

As mentioned above, it is not necessary to immobilize primer 4 on the support. If primer 4 is left free, the in situ PCR products yield the upper (primer I derived) strand upon denaturation:

```
5'-gcagcagtacgactagcataTCCGACctgcgtgtagcgcacgtaccggggtacgtagtcc  [SEQ ID NO: 9]
                         gactgctgGTCGGAcctgcatgctactgctatcg-3'.
```

This sequence is available for hybridization to fluorescently-labeled DNA or RNA for mRNA quantitation or genotyping.

EXAMPLE 7

Isolation of a feature from an array of the invention (Method 2)

As described above, laser-capture microdissection is performed in order to help orient a worker using the arrays of a set of arrays produced according to the invention, or to remove undesirable features from them. Alternatively, this procedure is employed to facilitate the cloning of selected features of the array that are of interest. The transfer of the nucleic acid molecules of a given feature or group of features from the array to a thin film of EVA or another heat-sensitive adhesive substance is performed as described above. Following those steps, the molecules are amplified and cloned as follows:

The transfer film and adherent cells are immediately resuspended in 40 µl of 10 mM Tris.HCl (pH 8.0), 1 mM EDTA and 1% Tween-20, and incubated overnight at 37° C. in a test tube, e.g. a polypropylene microcentrifuge tube. The mixture is then boiled for 10 minutes. The tubes are briefly spun (1000 rpm, 1 min.) to remove the film, and 0.5 µl of the supernatant is used for PCR. Typically, the sheets of transfer film initially applied to the array are small circular disks (diameter 0.5 cm). For more efficient elution of the after LCM transfer, the disk is placed into a well in a 96-well microliter plate containing 40 µl of extraction buffer. Oligonucleotide primers specific for the sequence of interest may be designed and prepared by any of the methods described above. PCR is then performed according to standard methods, as described in the above examples.

USE

The invention is useful for generating sets each comprising a plurality of copies of a randomly-patterned, immobilized (thus highly reusable) nucleic acid arrays from a first array upon which the molecules of a nucleic acid pool are randomly positioned quickly, inexpensively and from unique pools of nucleic acid molecules, such as biological samples. The sets of arrays, and members of such sets, produced according to the invention are useful in expression analysis (Schena, et al., 1996, *Proc. Nat. Acad. Sci. U.S.A.*, 93:10614–10619; Lockhart, et al., 1996, *Nature Biotechnology* 14:1675–1680) and genetic polymorphism detection (Chee et al., 1996, *Science*, 274(5287):610–614). They are also of use in DNA/protein binding assays and more general protein array binding assays.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method of producing a plurality of a nucleic acid array, comprising, in order, the steps of,
   a) providing a first nucleic acid array comprising a pool of nucleic acid molecules immobilized to a support with the nucleic acid molecules being randomly patterned, and amplifying in situ the nucleic acid molecules,
   b) transferring at least a subset of nucleic acid molecules produced by said amplifying is to a second support, and
   c) immobilizing said subset to said second support to form a second nucleic acid array, wherein the nucleic acid molecules of said second array occupy positions that correspond to those of said nucleic acid molecules from which they were amplified on said first array to produce said plurality.

2. The method according to claim 1, further comprising the step after step b) of repeating steps b) and c).

3. The method according to claim 2, further comprising the step, after step b) or a repetition thereof, of repeating step a).

4. The method according to claim 1, further comprising after step b) the step of transferring and immediately at least a subset of the molecules transferred to said second support to a third support.

5. The method according to claim 1, further comprising the step of amplifying said nucleic acid molecules of said second array.

6. The method according to claim 1, wherein said pool of nucleic acid molecules is prepared from RNA or DNA.

7. The method according to claim 6, wherein said pool of nucleic acid molecules comprises cDNA or genomic DNA.

8. The method according to claim 1, wherein said pool of said nucleic acid molecules is a library.

9. The method according to claim 1, wherein said pool of nucleic acid molecules is prepared by
   a) cloning genomic DNA or cDNA into a cloning site on a nucleic acid vector and
   b) subsequently cleaving said nucleic acid molecules from said vector, wherein said cloning site is flanked on either side by oligonucleotide sequences that will remain linked to said nucleic acid molecules after said cleaving of step b).

10. The method of claim 9, wherein said oligonucleotide sequences comprise recognition sites for a restriction enzyme(s).

11. The method according to claim 10, wherein subsequent cleavage of the nucleic acid molecules of said library to which said sites are linked with said enzyme(s) results in the release of pairs of oligonucleotide primers that comprise sequences unique to either end of each member of said library.

12. The method according to claim 10, wherein said recognition sites are those of type IIS restriction enzymes.

13. The method according to claim 1, wherein said support is semi-solid.

14. The method according to claim 13, wherein said semi-solid support is selected from the group that includes polyacrylamide, cellulose, polyamide (nylon) and cross-linked agarose, -dextran and -polyethylene glycol.

15. The method according to claim 1, wherein said amplifying of nucleic acid molecules of step a) is performed by polymerase chain reaction (PCR).

16. The method according to claim 1, wherein said immediately is performed using a covalent linker that is selected from the group that includes oxidized 3-methyl uridine, an acrylyl group and hexaethylene glycol.

17. The method according to claim 1, wherein said step of immobilizing includes hybridization of members of said pool to nucleic acid molecules that are covalently bound to said support.

18. The method according to claim 9, wherein said nucleic acid molecules bound to said support are synthetic oligonucleotides.

19. The method according to claim 1, wherein said transferring of step b) comprises contacting said first array with a support, such that at least a subset of said nucleic acid molecules produced by said amplifying of step a) are transferred to said support.

20. The method according to claim 1, wherein said transferring of step b) comprises the steps of
   i) contacting said first array with a carrier selected from the group that includes a cylindrical roller, a stamping device, a membrane and a support, such that at least a subset of said nucleic acid molecules produced by said amplifying of step a) are transferred to said carrier, and
   ii) subsequently contacting said carrier with a support.

21. A plurality of a nucleic acid array, wherein said plurality comprises
   a) a first template randomly-patterned, covalently immobilized nucleic acid array comprising a pool of nucleic acid molecules randomly immobilized on a support, and
   b) a second randomly-patterned, covalently immobilized nucleic acid array, wherein the nucleic acid molecules of said second array are nucleic acid amplification products of said pool and wherein said nucleic acid molecules of said second array occupy positions on said second array that correspond to those of said nucleic acid molecules from which they were amplified on said first array.

22. A method for determining the sequential order of genetic elements of a chromosome, comprising providing an immobilized nucleic acid array, comprising the steps of
   a) providing an immobilized chromosome,
   b) amplifying the nucleic acid sequences of said chromosome,
   c) contacting said amplified sequences with a support, such that a subset of nucleic acid molecules produced by said amplifying are retained by said support,
   d) immobilizing said nucleic acid molecules so retained to said support to form a first immobilized nucleic acid array, wherein the positions of the members of said array correspond to the positions of the DNA sequences from which they were amplified on said chromosome, and e) determining the order of genetic elements on said chromosome, wherein said ordering comprises identifying the features of said array and wherein the position of a first feature relative that of a second feature on said array corresponds to the position of a first genetic element relative to that of a second genetic element on said chromosome.

23. The method according to claim 22, wherein said amplifying is performed by PCR.

24. The method according to claim 22, wherein said identifying is performed using sequencing by hybridization (SBH), quantitative incremental fluorescent nucleotide addition sequencing (QIFNAS) or stepwise ligation and cleavage.

25. A method for localizing RNA molecules within a cell or a tissue section comprising providing an immobilized nucleic acid array, comprising the steps of a) providing an immobilized cell or a tissue section, b) reverse transcribing RNA molecules of said cell or said tissue section to produce an array of features comprising reverse transcripts, c) contacting said array with a support, such that at least a subset of said reverse transcripts are retained by said support, and d) immobilizing said reverse transcripts to said support to form an immobilized nucleic acid array, and e) localizing said RNA molecules, comprising identifying said features of said array, wherein the positions of said features on said array correspond to the positions of said RNA molecules in said cell or said tissue section.

26. The method according to claim 25 further comprising the step after step b) of amplifying said reverse transcripts.

27. The method according to claim 26, wherein said amplifying is performed by PCR.

28. The method according to claim 25, wherein said identifying is performed using sequencing by hybridization (SBH), quantitative incremental fluorescent nucleotide addition a sequencing (QIFNAS) or stepwise ligation and cleavage.

29. The method according to claims 22 or 25, further comprising the steps after step c) of i) amplifying the molecules of said first array by PCR and ii) contacting said first array with a second support, such that at least a subset of said amplified nucleic acid molecules are transferred to said support, and iii) immobilizing said nucleic acid molecules to said second support to form a second immobilized nucleic acid array, wherein the positions of the members of said second array correspond to the positions of said molecules from which they were amplified on said first array.

30. A method of obtaining a plurality of immobilized nucleic acid arrays, wherein the arrays of the plurality are derived from different nucleic acid pools, comprising the steps of a) providing a first immobilized nucleic array acid comprising a first pool of nucleic acid molecules that have linked to both ends oligonucleotide sequences each comprising a restriction enzyme(s) recognition site, such that cleavage of the nucleic acid molecules of said pool with said enzyme(s) results in the release of pairs of oligonucleotide primers that comprise sequences unique to either end of each member of said pool, b) amplifying by PCR the nucleic acid molecules of said array, c) contacting said first immobilized nucleic acid array with a support such that at least a subset of nucleic acid molecules produced by said amplifying are transferred to said support, d) immobilizing said nucleic acid molecules to said support to form a replica of said first immobilized nucleic acid array, wherein the positions of said nucleic acid molecules on said replica correspond to the positions of said nucleic acid molecules of said first array from which they were amplified, e) cleaving said nucleic acid molecules of said replica with said restriction enzyme(s), thereby forming an array of immobilized oligonucleotide primers that comprise sequences unique to either end of each feature of said first nucleic acid array, f) washing from said oligonucleotide primers the nucleic acid fragments released from them by said cleaving, g) contacting said primers with a second pool of nucleic acid molecules under conditions that permit hybridization of the nucleic acid molecules that are complementary, such that hybridization occurs between said oligonucleotide primers and the nucleic acid molecules of said second nucleic acid pool, h) amplifying the nucleic acid molecules of said second pool so hybridized to said primers, wherein said immobilized oligonucleotide primers to which they are hybridized serve to prime said amplifying, thereby forming an immobilized array of nucleic acid molecules of said second pool.

31. The method according to claim 30, wherein said amplifying is performed by PCR.

32. The method according to claim 30, wherein cycles of said steps c) through h) are repeated.

33. The method according to claim 30, further comprising the steps between steps d) and e) of i) amplifying in situ the nucleic acid molecules of said replica, and ii) contacting said replica with a second support, such that at least a subset of the nucleic acid molecules produced by said amplifying are transferred to said second support, iii) immobilizing the termini of said nucleic acid molecules to said second support to form a second replica of said first immobilized nucleic acid array, wherein the positions of nucleic acid molecules on said second replica correspond to the positions of the nucleic acid molecules of said replica from which they were amplified..

34. The method according to claim 30, wherein said different nucleic acid pools are obtained from different tissues of an individual organism.

35. The method according to claim 30, wherein said different nucleic acid pools are obtained from different individual organisms of a single species.

36. The method according to claim 30, wherein said different nucleic acid pools are obtained from organisms of different species.

37. The method according to claim 30, wherein said first and second pools of nucleic acid molecules are libraries.

38. The method of claim 1, wherein said method further comprises the step, after step c), of identifying a feature of a said first or second array.

39. The method of claim 38, wherein said identifying is performed using sequencing by hybridization (SBH), quantitative incremental fluorescent nucleotide addition sequencing (QIFNAS) or stepwise ligation and cleavage.

* * * * *

SEQUENCE LISTING

<160> NUMBER OF SEQ ID NOS: 9

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:T7 RNA
      polymerase binding sequence

<400> SEQUENCE: 1
taatacgact cactata                                                    17

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 2
tgcatgctat                                                            10

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 3
atagcatgca atgcatttac gtagc                                           25

<210> SEQ ID NO 4
<211> LENGTH: 32
<212> TYPE: DNA
<213> ORGANISM: Artificial Sequence

```
<220> FEATURE:
<223> OTHER INFORMATION: Description of Artificial Sequence:hypothetical
      sequence
<220> FEATURE:
<221> NAME/KEY: unsure
<222> LOCATION: (27)..(32)
<223> OTHER INFORMATION: n equals a, t, c or g.

<400> SEQUENCE: 4
gcagcagtac gactagcata tccgacnnnn nn                                      32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:hypothetical
      sequence
<220> FEATURE:
<221> NAME/KEY: unsure
<222> LOCATION: (27)..(32)
<223> OTHER INFORMATION: n equals a, t, c or g.

<400> SEQUENCE: 5
cgatagcagt agcatgcagg tccgacnnnn nn                                      32

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 6
tcggctcatc tgcatgctgc cagcagtcgg actacgtacc ccggtacgtg cgctacacgc        60
agcttt                                                                   66

<210> SEQ ID NO 7
<211> LENGTH: 88
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 7
gcagcagtac gactagcata tccgacctgc gtgtagcgca cgtaccgggg tacgtagtcc        60
gactgctggc agcatgcaga tgagccga                                           88

<210> SEQ ID NO 8
<211> LENGTH: 94
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 8
cgatagcagt agcatgcagg tccgaccagc agtcggacta cgtaccccgg tacgtgcgct        60
acacgcaggt cggatatgct agtcgtactg ctgc                                    94

<210> SEQ ID NO 9
<211> LENGTH: 94
<212> TYPE: DNA
<213> ORGANISM: Artificial Sequence
```

-continued

```
<220> FEATURE:
<223> OTHER INFORMATION: Description of Artificial Sequence:hypothetical
      sequence

<400> SEQUENCE: 9
gcagcagtac gactagcata tccgacctgc gtgtagcgca cgtaccgggg tacgtagtcc      60
gactgctggt cggacctgca tgctactgct atcg                                 94
```